United States Patent
Roggenbuck

(10) Patent No.: US 11,549,952 B2
(45) Date of Patent: Jan. 10, 2023

(54) METHOD FOR THE DIAGNOSIS OF ACUTE PANCREATITIS (AP) BY DETECTION OF GLYCOPROTEIN 2 ISOFORM ALPHA (GP2A)

(71) Applicant: GA GENERIC ASSAYS GMBH, Dahlewitz (DE)

(72) Inventor: Dirk Roggenbuck, Strausberg (DE)

(73) Assignee: GA GENERIC ASSAYS GMBH, Dahlewitz (DE)

( * ) Notice: Subject to any disclaimer, the term of this patent is extended or adjusted under 35 U.S.C. 154(b) by 128 days.

(21) Appl. No.: 16/331,608

(22) PCT Filed: Sep. 26, 2017

(86) PCT No.: PCT/EP2017/074405
§ 371 (c)(1),
(2) Date: Mar. 8, 2019

(87) PCT Pub. No.: WO2018/055209
PCT Pub. Date: Mar. 29, 2018

(65) Prior Publication Data
US 2019/0219596 A1    Jul. 18, 2019

(30) Foreign Application Priority Data
Sep. 26, 2016 (EP) .................................... 16190594

(51) Int. Cl.
*G01N 33/53* (2006.01)
*G01N 33/68* (2006.01)
*G01N 33/574* (2006.01)

(52) U.S. Cl.
CPC ... *G01N 33/6893* (2013.01); *G01N 33/57438* (2013.01); *G01N 33/57446* (2013.01); *G01N 2800/067* (2013.01)

(58) Field of Classification Search
None
See application file for complete search history.

(56) References Cited

U.S. PATENT DOCUMENTS

2006/0105419 A1* 5/2006 Blankenberg ........ G01N 33/573
435/25
2007/0275422 A1* 11/2007 Lowe ............... G01N 33/57438
435/7.23

OTHER PUBLICATIONS

Banks et al., Clinical Roundtable momograph, The Management of Acute and Chronic Pancreatitis, Gastroenterology & Hepatology, vol. 6, Iss. 2. Suppl. 5, Feb. 2010, pp. 1-16. (Year: 2010).*
Dirk Roggenbuck et al:"Serological diagnosis and prognosis of severe acute pancreatitis by analysis of serum glycoprotein 2", Clinical Chemistry and Laboratory Medicine,Jan. 12, 2016.
Fukuoka S-I: "Molecular cloning and sequences of cDNAs encoding alpha (large) and beta (small) isoforms of human pancreatic zymogen granule membrane-associated protein", Biochimica Et Biophysica Acta. Gene Structure and Expression, Elsevier, Amsterdam, NL, vol. 1491, No. 1-3, Apr. 25, 2000, pp. 376-380.
Wong S M E et al: "Sequence of the cDNA encoding human GP-2, the major membrane protein in the secretory granule of the exocrine pancreas", Gene, Elsevier, Amsterdam, NL, vol. 171, No. 2, Jun. 1, 1996.
Ying Hao et al:"Determination of Plasma Glycoprotein 2 Levels in Patients With Pancreatic Disease", Arch Pathol Lab Med-Vol, vol. 128, Jan. 1, 2004.
International Search Report for International appl. No. PCT/EP2017/074405, dated Dec. 3, 2018.

* cited by examiner

*Primary Examiner* — Gary Counts
(74) *Attorney, Agent, or Firm* — Agris & von Natzmer LLP; Joyce von Natzmer

(57) ABSTRACT

The invention relates to an in vitro method for the diagnosis of acute pancreatitis (AP) in a subject by detection of Glycoprotein 2 isoform alpha (GP2a) protein. In particular the invention pro-vides an in vitro method for the diagnosis of acute pancreatitis (AP) in a subject by detection of Glycoprotein 2 isoform alpha (GP2a) protein, comprising providing a sample of a human subject exhibiting symptoms of having pancreatic disease, wherein said sample is obtained from the subject within 72 hours of the appearance of said symptoms, providing an affinity reagent directed against GP2a, contacting said sample with said affinity reagent thereby capturing GP2a from said sample, and determining the concentration of GP2a from said sample, wherein determining a concentration of GP2a in said sample that is greater than the average concentration of GP2a in control samples, such as in a group of healthy individuals, indicates the presence of AP and the absence of one or more of chronic pancreatitis, pancreatic cancer, gastrointestinal cancer, liver cancer, neuroendocrine tumor, sarcoma, peptic ulcer or peritonitis. The invention further provides a kit and a system developed for carrying out the claimed method and determining the concentration of GP2a and performing an automated analysis of one or more samples.

14 Claims, 7 Drawing Sheets
Specification includes a Sequence Listing.

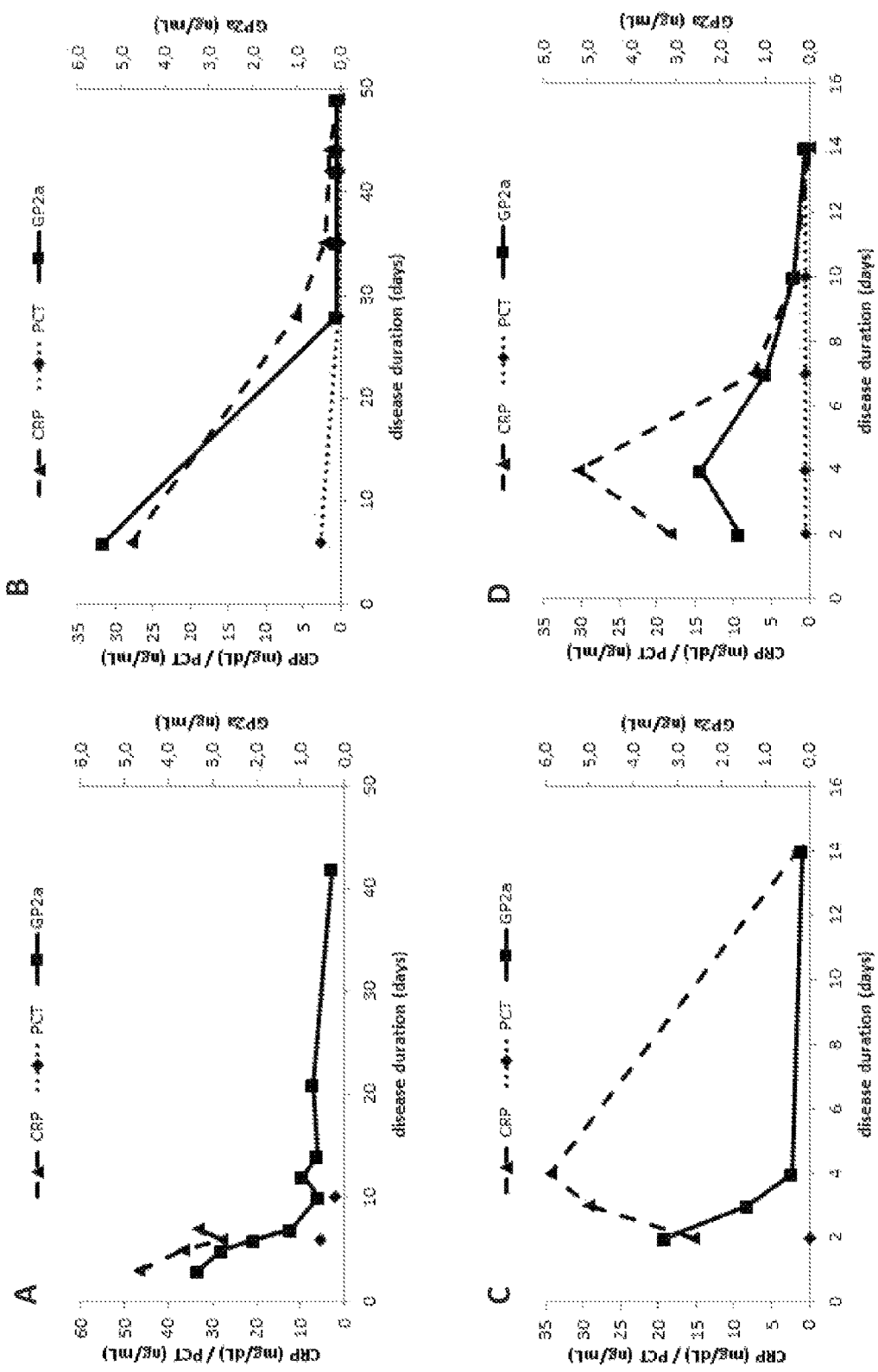
Figure 7A-D

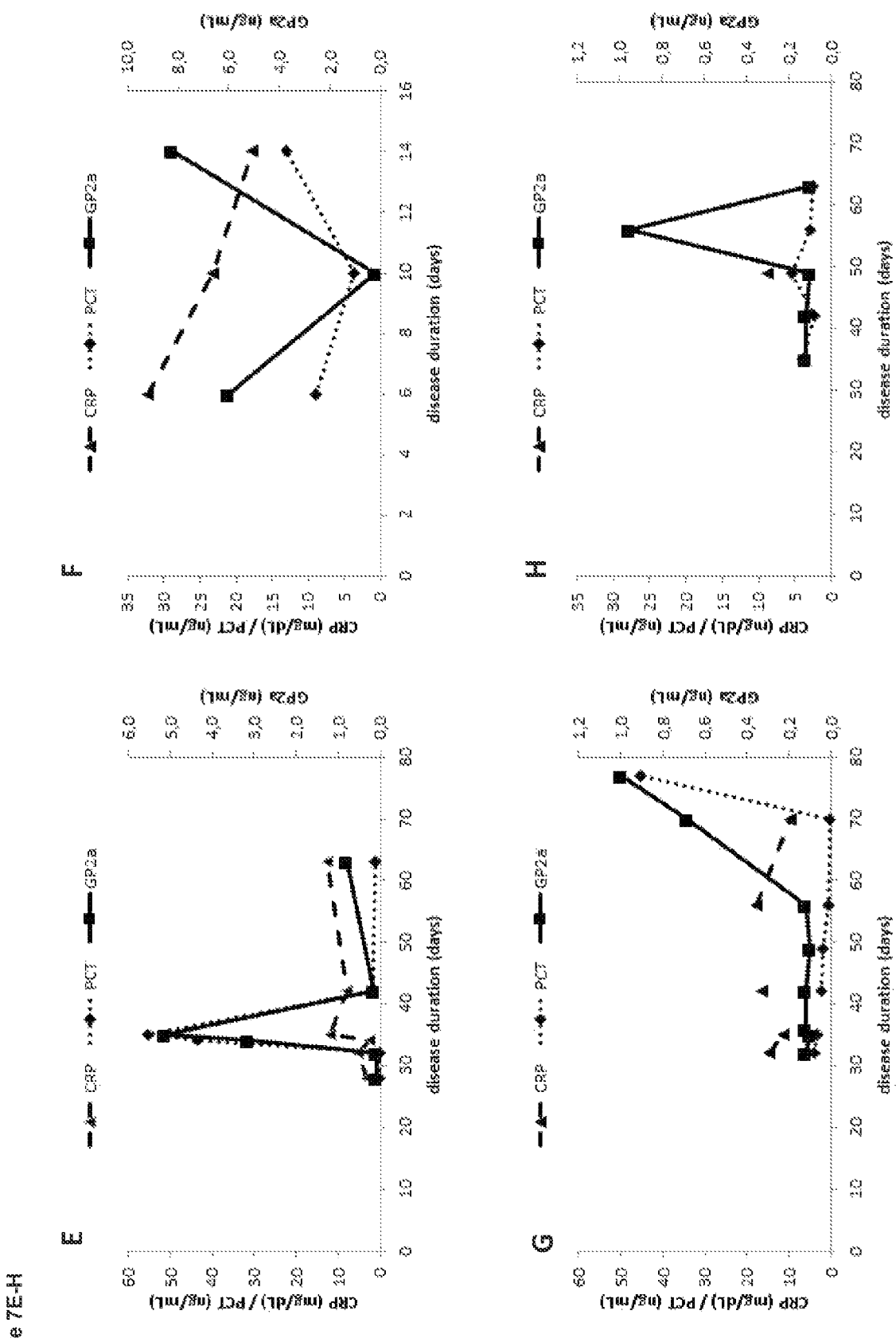
Figure 7E-H

METHOD FOR THE DIAGNOSIS OF ACUTE PANCREATITIS (AP) BY DETECTION OF GLYCOPROTEIN 2 ISOFORM ALPHA (GP2A)

CROSS-REFERENCE TO RELATED APPLICATIONS

This is the U.S. national stage of International application PCT/EP2017/074405, filed Sep. 26, 2017 designating the United States and claiming priority to European patent application EP 16190594.8, filed Sep. 26, 2016.

INCORPORATION OF SEQUENCE LISTING

The sequence listing filed as a text file as part of International application PCT/EP2017/074405, filed Sep. 26, 2017 is hereby incorporated by reference. An extra copy of this text file named "eolf-seql.txt", which is 23 kilobytes (measured in MS-WINDOWS), dated Mar. 7, 2019 was downloaded from WIPO and is submitted herewith via the USPTO EFS system.

The invention relates to an in vitro method for the diagnosis of acute pancreatitis (AP) in a subject by detection of Glycoprotein 2 isoform alpha (GP2a) protein. In particular the invention provides an in vitro method for the diagnosis of acute pancreatitis (AP) in a subject by detection of Glycoprotein 2 isoform alpha (GP2a) protein, comprising providing a sample of a human subject exhibiting symptoms of having pancreatic disease, wherein said sample is obtained from the subject within 72 hours of the appearance of said symptoms, providing an affinity reagent directed against GP2a, contacting said sample with said affinity reagent thereby capturing GP2a from said sample, and determining the concentration of GP2a from said sample, wherein determining a concentration of GP2a in said sample that is greater than the average concentration of GP2a in control samples, such as in a group of healthy individuals, indicates the presence of AP and the absence of one or more of chronic pancreatitis, pancreatic cancer, gastrointestinal cancer, liver cancer, neuroendocrine tumor, sarcoma, peptic ulcer or peritonitis. The invention further provides a kit and a system developed for carrying out the claimed method and determining the concentration of GP2a and performing an automated analysis of one or more samples.

BACKGROUND OF THE INVENTION

The serological diagnosis of acute pancreatitis (AP), an acute inflammatory condition of the pancreas and the main cause for hospitalization in case of acute abdominal pain in developed countries like the United States [1], is still a laboratory challenge.[2] The search for serological parameters for the diagnosis of AP therefore continues unabatedly.

The incidence of AP, which remains a life-threatening disease with a mortality rate of up to 40% in severe AP, ranges from 17.5 to 73.4 cases per 100,000 individuals globally.[2] Although the pathophysiology of AP is not understood entirely yet, it is now widely acknowledged that premature intra-pancreatic activation of digestive proenzymes in particular trypsinogen stored in pancreatic vesicles called zymogen granules (ZG) by cathepsin B or other active peptides plays a pivotal role.[3-7] Thus, AP onset is characterized by acinar cell injury which results in an impaired polarity of proenzyme secretion and the subsequent extrusion of ZG and release of its content across the basolateral membrane into the interstitium.[4] The ensuing cellular inflammatory response mediated by macrophages and neutrophils up to the formation of neutrophil extracellular traps can lead to a systemic inflammatory response syndrome and even to systemic shock.[8] Thus, the leakage of ZG-related molecules like pancreatic lipase and amylase or trypsinogen as well as the induction and release of inflammatory cytokines such as interleukin 6 and 8 (CXC8L) by immune cells involved into the blood stream generates a plethora of potential serological AP-specific markers.[9] However, despite the continuous identification of novel potential biomarkers by emerging proteomic technologies, serum lipase analysis is still the only serological tool with high strength of evidence for the diagnosis of disease according to the revised 2012 Atlanta Classification of AP.[10] Elevated levels should exceed 3 times the upper limit of the normal. Serum lipase analysis is preferred to amylase testing nowadays due to its increased sensitivity.[11] However, false positive lipase testing has been reported in 51 (23.2%) non-AP patients mainly with decompensated cirrhosis and renal failure by a prospective analysis of 221 consecutive patients with elevated lipase findings recently.[12]

Of note, serum C-reactive protein (CRP) is used for severity assessment of AP in which levels above 150 mg/dL (14,286 nmol/L) are indicative for a severe course of AP.[13] Furthermore, procalcitonin (PCT) is recommended as a useful marker in early prediction of severe AP, pancreatic necrosis, and organ failure.[10; 14]

Additional serum AP markers like pancreatic isoamylase, pancreatic elastase, trypsin, urinary trypsinogen activated peptide, serum trypsinogen 2 and 3, phospholipase A2, and activation peptide of carboxypeptidase B have been added to the ever growing list of putative AP markers.[2; 9]. Due to a variety of reasons, such as inferior diagnostic accuracy or laborious testing, these novel markers have been not widely implemented into routine diagnostics yet.

In the ongoing search for novel AP-specific parameters, a well-characterized animal model of AP revealed elevated major ZG membrane glycoprotein 2 (GP2) in serum as a potential marker for AP.[15] Like digestive proenzymes, GP2 is released into the pancreatic duct upon exocrine pancreatic stimulation.[16] In contrast, however, GP2 is linked to the ZG membrane by a glycosyl-phosphatidylinositol (GPI) anchor cleavable by phospholipase C.[17; 18]

Of note, two isoforms of GP2, termed alpha (GP2a) and beta (GP2b), both expressed at equal levels in the pancreas, were described.[19; 27] The two variants of GP2 are produced in humans due to alternative splicing. Besides the large form of GP2, containing 537 amino acids and termed alpha, a shorter beta form exists which comprises only 390 amino acids. Currently, four isoforms of GP2 have been described (see tables 1 to 3 of the detailed description of the invention).

Interestingly, GP2 obviously released via the basolateral membrane of acinus cells into the bloodstream demonstrated a slower clearance in serum compared with lipase and amylase levels in the cerulean-induced AP in rats.[15] Later on, significantly higher levels of human GP2 could be detected by a research enzyme-linked immunosorbent assay (ELISA) in patients with AP compared to controls.[20] Remarkably, the quantification of plasma GP2 showed a better assay accuracy and at least 1 day longer increased levels in patients with AP compared to the established lipase and amylase testing.

However, elevated concentrations of GP2 were also observed in patients with chronic pancreatitis (CP) and pancreatic cancer (PCa) by this assay. US2007275422 describes a method for determining whether a human subject has a pancreatic disease, including acute and chronic pancreatitis and pancreatic cancer. These latter findings, however, questioned the association of serum GP2 with the fulminant inflammation characteristic for AP and consequently the clinical usefulness of GP2 as an AP-specific marker.

There is an urgent need to establish improved technical means for detecting serological markers that are specific for AP and allow the diagnosis of AP with a higher accuracy as compared to the tests used in the art. Methods for differentiating between AP and other pancreatic diseases, such as CP and PCa, especially at early disease stages, are urgently needed.

SUMMARY OF THE INVENTION

In light of the prior art the technical problem underlying the present invention is the provision of means for diagnosing acute pancreatitis (AP) that are more accurate and preferably enable an earlier diagnosis than those means known in the prior art. A further problem to be solved may be considered the provision of means for differentiating between AP and other pancreatic diseases, including chronic pancreatitis, pancreatic cancer, gastrointestinal cancer, liver cancer, neuroendocrine tumor, sarcoma, peptic ulcer or peritonitis, in particular at an early stage of the disease or at an early time point after symptoms exist.

The problem is solved by the invention according to the independent claims. Preferred embodiments are provided in the dependent claims.

The invention therefore relates to an in vitro method for the diagnosis of acute pancreatitis (AP) in a subject by detection of Glycoprotein 2 isoform alpha (GP2a) protein, comprising:
  providing a sample of a human subject exhibiting symptoms of having pancreatic disease, wherein said sample is obtained from the subject within 72 hours of the appearance of said symptoms,
  providing an affinity reagent directed against GP2a,
  contacting said sample with said affinity reagent thereby capturing GP2a from said sample, and
  determining the concentration of GP2a from said sample,
  wherein determining a concentration of GP2a in said sample that is greater than the concentration of GP2a in one or more control samples, such as in a group of healthy individuals, indicates the presence of AP and the absence of one or more of chronic pancreatitis, pancreatic cancer, gastrointestinal cancer, liver cancer, neuroendocrine tumor, sarcoma, peptic ulcer or peritonitis.

It was at the time of the invention entirely unknown that detection of GP2a could be used for differentiating patients that suffer from AP from patients suffering from other pancreatic diseases or diseases affecting the pancreas, including chronic pancreatitis, pancreatic cancer, gastrointestinal cancer, liver cancer, neuroendocrine tumor, sarcoma, peptic ulcer or peritonitis.

In particular, the method of the present invention provide means for determining, at an early point in time, such as when symptoms are classified as acute symptoms of pancreatic disease, the presence of AP, such that the presence of other pancreatic diseases can be ruled out. In light of the prior art, which teaches generally that multiple pancreatic diseases are to be assessed via GP2 levels, the present invention represent an unexpected finding.

Previous reports [20] had indicated that GP2 is elevated in patients with PA, chronic pancreatitis and pancreatic cancer to a similar extent, which did not make it possible to differentiate between the diseases. Therefore it is even more surprising, that specific detection of GP2a, preferably in contrast to the total amount of GP2 (GP2t), allows differentiation between AP and other pancreatic diseases. The present invention therefore represents a substantial improvement of the technical means available for serological diagnosis of AP in patients with diffuse symptoms associated with various pancreatic diseases or other diseases affecting the pancreas.

Detection of GP2t levels in samples of human subjects suffering from AP symptoms for the diagnosis of AP results in a higher number of patients falsely diagnosed as suffering from AP as compared to detection of GP2a in the same samples. Detection of GP2a therefore provides a much higher specificity as compared to the detection of GP2t, with a lower false positive rate in all control groups, consisting of healthy individuals and patients suffering from pancreatic diseases or diseases affecting the pancreas, including, without limitation, chronic pancreatitis, pancreatic cancer, gastrointestinal cancer, liver cancer, neuroendocrine tumor, sarcoma, peptic ulcer or peritonitis. GP2a testing proofed to be superior in terms of diagnostic accuracy as compared to all other serological tests available for the diagnosis of AP.

According to the present invention, the sample used for determining the concentration of GP2a is obtained from the subject within 72 hours from appearance of the symptoms. It was entirely surprising, that GP2a levels are specifically elevated in AP patients at this early time point after occurrence of disease symptoms, and that this is not the case for other pancreatic diseases or diseases affecting the pancreas. The possibility of earlier diagnosis of AP and exclusion of other diseases, as enabled by the in vitro method according to the present invention, has important implications on the therapeutic interventions to be initiated after receiving the patient and performing in vitro diagnosis and therefore will greatly contribute to improved treatment of patients suffering from AP.

It is particularly surprising that isolation of the sample used in the method of the present invention, when occurring within 72 hours after appearance of first symptoms, allows the differentiation of acute pancreatitis (AP) from other pancreatic diseases such as chronic pancreatitis (CP) or pancreatic cancer, since it has been shown that in AP the GP2 levels remain abnormally elevated for at least 5 days from occurrence of the first symptoms [20]. Furthermore, even if a chronic or progressive disease such as CP or pancreatic cancer is suspected, the method of the present invention should be performed rapidly after occurrence of the first symptoms, at least within 72 hours, to be able to exclude that the patient is suffering from AP instead of the suspected chronic or progressive diseases.

As GP2a levels in samples of AP patients with disease duration beyond the 10th day of appearance of disease symptoms are not significantly different from those in samples of patients suffering from pancreatic diseases or diseases affecting the pancreas, it was the more surprising that the GP2a levels in samples from AP patients until the 3rd day of disease duration, which means within 72 hours of appearance of said symptoms, are significantly elevated in comparison with all control groups including healthy individuals and patients suffering from pancreatic diseases or diseases affecting the pancreas, including, without limitation, chronic pancreatitis, pancreatic cancer, gastrointestinal cancer, liver cancer, neuroendocrine tumor, sarcoma, peptic ulcer or peritonitis.

In a preferred embodiment of the in vitro method according to the present invention, determining a concentration of GP2a in said sample that is greater than the concentration of GP2a in one or more control samples, such as in a group of healthy individuals, indicates the presence of AP and the absence of chronic pancreatitis and pancreatic cancer.

It was entirely surprising that the serological method of the present invention allows to differentiate between AP and chronic pancreatitis and pancreatic cancer at the early disease stage within 72 hours from occurrence of the disease symptoms, as the symptoms caused by these diseases are very similar and a differential diagnosis by serological means known in the art was not possible and therefore required diagnostic imaging techniques. Especially considering that chronic pancreatitis and pancreatic cancer were typically bundled into a single diagnostic determination of AP and chronic pancreatitis and pancreatic cancer based on GP2 levels, it is particularly surprising that GP2a enables differentiation from these diseases when measured at an early time point.

In another preferred embodiment of the method, determining a concentration of GP2a greater than 0.2 ng/ml indicates the presence of AP and the absence of one or more of chronic pancreatitis, pancreatic cancer, gastrointestinal cancer, liver cancer, neuroendocrine tumor, sarcoma, peptic ulcer or peritonitis.

It is a great advantage of the in vitro method according to the present invention that determining a concentration of GP2a in a sample of a human subject exhibiting symptoms of having AP allows diagnosis of the presence AP and the absence of other pancreatic diseases or disease affecting the pancreas, if the concentration of GP2a is greater than 0.2 ng/ml. Comparison of the determined GP2a concentration to a reference value is a very efficient and user friendly criterion for diagnosis and allows fast decision making according to the outcome of the method according to the present invention.

In another preferred embodiment of the method determining a concentration of GP2a greater than 0.7 ng/ml indicates the presence of AP and the absence of one or more of chronic pancreatitis, pancreatic cancer, gastrointestinal cancer, liver cancer, neuroendocrine tumor, sarcoma, peptic ulcer or peritonitis.

In another preferred embodiment of the method of determining a concentration of GP2a greater than a threshold value in the range of 0.2-1.0 ng/ml indicates the presence of AP and the absence of one or more of chronic pancreatitis, pancreatic cancer, gastrointestinal cancer, liver cancer, neuroendocrine tumor, sarcoma, peptic ulcer or peritonitis.

In further preferred embodiments of the present invention the threshold region can range from a value such as 0.2-1.5 ng/ml, 0.3-1.3 ng/ml, 0.4-1.1 ng/ml, 0.5 to 0.9 ng/ml, 0.2-1.0 ng/ml, 0.3-1.0 ng/ml, 0.4-1.0 ng/ml, 0.5-1.0 ng/ml, 0.6-1.0 ng/ml, 0.7-1.0 ng/ml, 0.8-1.0 ng/ml, 0.9-1.0 ng/ml, 0.2-0.9 ng/ml, 0.2-0.8 ng/ml, 0.2-0.7 ng/ml, 0.2-0.6 ng/ml, 0.2 0.5 ng/ml, 0.2-0.4 ng/ml, or 0.2-0.3 ng/ml.

In one aspect the invention relates to a method for the diagnosis of acute pancreatitis (AP) in a subject by detection of Glycoprotein 2 isoform alpha (GP2a) protein, wherein Glycoprotein 2 isoform alpha (GP2a) comprises or consists of a protein:
   a) with an amino acid sequence according to SEQ ID NO 1 or 2,
   b) a truncated amino acid sequence according to SEQ ID NO 1 or 2, with no more than 50 amino acids lacking from the N and/or C terminus of the sequence, or
   c) an amino acid sequence of more than 80%, more than 85%, more than 90% or more preferably more than 95% sequence identity to a) or b).

The isoforms of GP2 also relate to those of substantially the same amino acid sequence as those explicitly listed. This refers to one or more amino acid sequence that is similar, but not identical to, the amino acid sequence provided explicitly herein.

Variation in length of the amino acid sequences and encoding nucleic acids as described herein is also encompassed by the present invention. A skilled person is capable of providing artificial amino acid sequence variants that are longer or shorter than the specific sequences of SEQ ID NO 1 to 2, which will still exhibit sufficient similarity to the natural forms in order to provide the diagnostic outcomes described herein. For example, shorter variants of the longer isoforms (SEQ ID NO 1 or 2) comprising 10, 20, 30, 40 or 50 amino acids less than the full length form may also enable effective diagnostic outcomes, as described herein.

In a further embodiment of the invention as described herein, the affinity reagent specifically binds GP2a,
   wherein GP2a preferably comprises or consists of a protein
     a) with an amino acid sequence according to SEQ ID NO 1 or 2,
     b) a truncated amino acid sequence according to SEQ ID NO 1 or 2, with no more than 50 amino acids lacking from the N and/or C terminus of the sequence, or
     c) an amino acid sequence of more than 80%, more than 85%, more than 90% or more preferably more than 95% sequence identity to a) or b),
   with no binding or negligible binding to Glycoprotein 2 isoform beta (GP2b), preferably according to SEQ ID NO 3 or 4.

The invention relates to the surprising and unexpected finding that different isoforms of the GP2 protein, GP2a and GP2b, are differentially regulated during AP and that detection of GP2a results in higher diagnostic accuracy as compared to detection of GP2b or total GP2.

The isoforms of GP2 also relate to those of substantially the same amino acid sequence as those explicitly listed. This refers to one or more amino acid sequence that is similar, but not identical to, the amino acid sequence provided explicitly herein.

Variation in length of the amino acid sequences and encoding nucleic acids as described herein is also encompassed by the present invention. A skilled person is capable of providing artificial amino acid sequence variants that are longer or shorter than the specific sequences of SEQ ID NO 1 to 4, which will still exhibit sufficient similarity to the natural forms in order to provide the diagnostic outcomes described herein. For example, shorter variants of the longer isoforms (SEQ ID NO 1 or 2) comprising 10, 20, 30, 40 or 50 amino acids less than the full length form may also enable effective diagnostic outcomes, as described herein. For example, longer variants of the shorter isoforms (SEQ ID NO 3 or 4) comprising 10, 20, 30, 40 or 50 amino acids of GP2 sequence more than the natural length form may also enable effective diagnostic outcomes, as described herein.

In one aspect of the invention, said affinity reagent is a monoclonal antibody. It was beneficial to isolate an antibody that is completely specific to GP2a. Antibodies with such properties were completely unknown in the art and it was thought that the sequence that differentiates GP2a and GP2b does not contain suitable epitopes to generate specific antibodies. Therefore, it was surprising that in one embodiment of the present invention the affinity reagent directed against GP2a is a monoclonal antibody.

In a further embodiment of the present invention, said antibody binds specifically binds GP2a,
  wherein GP2a preferably comprises or consists of a protein
    a) with an amino acid sequence according to SEQ ID NO 1 or 2,
    b) a truncated amino acid sequence according to SEQ ID NO 1 or 2, with no more than 50 amino acids lacking from the N and/or C terminus of the sequence, or
    c) an amino acid sequence of more than 80%, more than 85%, more than 90% or more preferably more than 95% sequence identity to a) or b),
  with no binding or negligible binding to Glycoprotein 2 isoform beta (GP2b), preferably according to SEQ ID NO 3 or 4, in both native and denaturated sample conditions.

It was completely unexpected that it is possible to generate monoclonal antibody that shows high binding affinity and specificity to GP2a and does not show any cross-reactivity with GP2b. It is surprising that the portion of GP2a that is not contained in GP2b contains epitopes that are capable of generating highly specific monoclonal antibodies. It is a great advantage of this embodiment of the present invention that the monoclonal antibody does not only specifically bind to GP2a but not to GP2b under native conditions, but also under denaturated sample conditions, which allows for more flexibility in handling the sample material before performing the in vitro method according to the present invention, as the handling and processing of the sample does not necessarily require that the molecules in the sample remain in their native state. This is important for the process of sample preparation for analysis with the method of the present invention, in terms of storage conditions and buffer conditions.

In a further embodiment the method as described herein is conducted as an Enzyme Linked Immunosorbent Assay (ELISA), wherein said affinity reagent is immobilized on a solid surface before contacting said sample. It is a great advantage of the method according to present invention that it can be carried out as an ELISA, which is a conventional and routine laboratory technique that can be carried out in almost every diagnostic laboratory. As the method can be conducted as an ELISA, complicated diagnostic procedures such as endoscopies or biopsy analysis can be avoided and thereby a greater target group of people is enabled to execute the method according to the present invention.

The novel GP2a ELISA according to the present invention is a better diagnostic tool for the differential diagnosis of patients exhibiting symptoms of AP for indicating the presence of AP and the absence of other pancreatic diseases or diseases affecting the pancreas and proofed to be superior in terms of diagnostic accuracy and assay performance as compared to all other serological methods available for the diagnosis of AP including an ELSIA for GP2t. Another advantage of the GP2a ELISA according to the present invention is that it generates higher positive likelihood ratios and has a much lower rate of false positive results as compared to an ELISA against GP2t.

The GP2a ELISA according to the present invention shows good linearity. Furthermore, the GP2a ELSISA according to the present invention showed excellent intra-assay and inter-assay coefficients of variation making it a robust and reproducible in vitro method for the diagnosis of AP. The GP2a ELISA according to the present invention has very good recovery of GP2a of the GP2a present in a sample, demonstrating that this method is a reliable diagnostic test. Another great advantage of the GP2a ELISA according to the present invention is the robustness of the method towards interference of the generated signal with other molecules present in the sample. To date no molecule was identified that significantly interferes with the signal generated by the ELISA method according to the present invention, making it a reliable in vitro method for diagnosis of AP.

In one embodiment the method of the present invention is characterized in that the determination of GP2a concentration is carried out by
  a) capturing GP2a from the sample via the GP2a affinity reagent that is immobilized to the solid surface,
  b) treating said captured GP2a with a labeled secondary affinity reagent directed to GP2,
  c) detecting a signal emitted from said labeled secondary affinity reagent directed to GP2, and
  d) comparing the signal obtained from said labeled secondary affinity reagent with the signal from one or more control samples of pre-determined GP2a concentration.

It is a great advantage of this embodiment of the present invention that the concentration of GP2a in a sample can be carried out by comparing the signal emitted from the labeled secondary affinity reagent that has captured GP2a within the sample to the signal emitted from the said secondary affinity reagents from one or more control samples of pre-determined GP2a concentration. Such control samples can easily generated at the time of performing the method by using recombinant GP2a. This allows for determination of the GP2a concentration in a routine laboratory procedure that only requires standard laboratory equipment.

The fact that the affinity reagent that is specific to the GP2a isoform is immobilized allows the removal of all other sample components except GP2a from the surface coupled to the GP2a affinity reagent by washing the solid surface after capturing the GP2a molecules present in the sample. As there is no other GP2 than GP2a present on the solid surface after washing away all other sample components, it is possible to use a secondary affinity reagent that is not specific to GP2a but just has to be able to recognize any labeled GP2 affinity reagent. Such affinity reagents are known in the art and are readily available, which is a great advantage for making the present invention widely available.

In a preferred embodiment of the present invention, said signal is preferably obtained from horseradish peroxidase conjugated to the secondary affinity reagent. Horeseradish peroxidase (HRP) is used in biochemistry applications primarily for its ability to amplify a weak signal and increase detectability of a target molecule. Its presence is be made visible by using a substrate that, when oxidized by HRP using hydrogen peroxide as the oxidizing agent, yields a characteristic change that is detectable by spectrophotometric methods. Numerous substrates for the horseradish peroxidase enzyme have been described and commercialized to exploit the desirable features of HRP. Horseradish peroxidase is also commonly used in techniques such as ELISA and Immunohistochemistry due to its monomeric nature and the ease with which it produces colored products. Horseradish peroxidase is ideal in many respects for these applications because it is smaller, more stable, and less expensive than other popular alternatives. It also has a high turnover rate that allows generation of strong signals in a relatively short time span.

The GP2a and GP2t concentrations and cut-offs for GP2a and GP2t disclosed herein refer preferably to measurements of the protein level of GP2a and PG2t in a serum sample obtained from a patient by means of the ELISA measurements of GP2a and PG2t described herein. Preferably, the ELISA measurements for determining the concentration of GP2a and GP2t are carried out as described in the EXAMPLES section of the present patent application.

Accordingly, the values disclosed herein may vary to some extent depending on the detection/measurement method employed and the specific values disclosed herein are intended to also read on the corresponding values determined by other methods or modification of the methods disclosed herein.

According to a further embodiment of the method of the present invention, the sample is a blood sample, a plasma sample, a serum sample, a saliva sample, a urine sample, a stool sample, a tears sample, a sample from pure pancreatic juices or duodenal juices, a tissue sample or a cellular extract. Preferably, the sample is a blood sample, a plasma sample or a serum sample, most preferably a serum sample.

In one embodiment the invention additionally comprises informing the patient of the results of the diagnostic method described herein.

The invention further provides a kit for the diagnosis of of acute pancreatitis (AP) in a subject by detection of Glycoprotein 2 isoform alpha (GP2a) protein, comprising:
   a) an affinity reagent directed against GP2a and a solid surface for immobilization of said affinity reagent, or an affinity reagent directed against GP2a immobilized to a solid surface,
   b) a labeled secondary affinity reagent directed to GP2 and means for detecting the signal emitted from said label, and
   c) computer software configured for determining the concentration of GP2a captured from a sample via an affinity reagent directed against GP2a, wherein said software is further configured for determining whether the GP2a concentration in said sample is greater than the average concentration of GP2a in one or more control samples, such as in a group of healthy individuals.

Preferably, the invention relates to a kit for the diagnosis of acute pancreatitis (AP) in a subject by detection of Glycoprotein 2 isoform alpha (GP2a) protein, comprising:
   a) an affinity reagent directed against GP2a and a solid surface for immobilization of said affinity reagent, or an affinity reagent directed against GP2a immobilized to a solid surface,
   b) a labelled secondary affinity reagent directed to GP2 and means for detecting the signal emitted from said label, and
   c) computer software configured for determining the concentration of GP2a captured from a sample via an affinity reagent directed against GP2a, wherein said software is further configured for determining whether the GP2a concentration in said sample is above or below 0.7 ng/mL.

The combination of all reagents required for performing the in vitro method according to the present invention in a format appropriate for carrying out the method is motivated only by the novel and surprising finding of the present invention. The combination of an affinity reagent directed against GP2a and a solid surface for immobilization of said affinity reagent, or an affinity reagent directed against GP2a immobilized to a solid surface, a labeled secondary affinity reagent directed to GP2 and means for detecting the signal emitted from said label, and computer software configured for determining the concentration of GP2a captured from a sample via an affinity reagent directed against GP2a, wherein said software is further configured for determining whether the GP2a concentration in said sample is greater than the average concentration of GP2a in one or more control samples, such as in a group of healthy individuals as such is therefore to be considered an unexpected development of the art. There exists no suggestion in the relevant literature that the provision of a kit comprising said components should have been developed.

The computer software according to the preferred embodiment of the present invention is executed by an optionally networked computer processing device configured to perform executable instructions to apply a model or algorithm for analyzing the signals generated by the labeled secondary affinity reagents directed against GP2.

In another preferred embodiment, the kit is characterized in that the computer software further comprises a software module to designate a treatment regimen for the individual. Accordingly, it is possible that the computer software of the kit not only provides a diagnosis on the result of the method carried out with the help of the kit, but also provides information with respect to the treatment regimen that should be administered to the patient due to the result of the method of the present invention.

The methods of the present invention may in part be computer-implemented. For example, the step of comparing the detected level of GP2a with a reference level can be performed in a computer system. In the computer-system, the determined level of the GP2a can be combined with other marker levels and/or parameters of the subject. In the computer-system, the determined level of the GP2a can be combined with other marker levels and/or parameters of the subject in order to calculate a score, which is indicative for the diagnosis, prognosis, risk assessment and/or risk stratification. For example, the determined values may be entered (either manually by a health professional or automatically from the device(s) in which the respective marker level(s) has/have been determined) into the computer-system. The computer-system can be directly at the point-of-care (e.g. primary care, intensive care unit or emergency department) or it can be at a remote location connected via a computer network (e.g. via the internet, or specialized medical cloud-systems, optionally combinable with other IT-systems or platforms such as hospital information systems (HIS)). Typically, the computer-system will store the values (e.g. GP2a level or parameters such as age, blood pressure, weight, sex, etc. or clinical scoring systems) on a computer-readable medium and calculate the score based-on pre-defined and/or pre-stored reference levels or reference values. The resulting score will be displayed and/or printed for the user (typically a health professional such as a physician). Alternatively or in addition, the associated prognosis, diagnosis, assessment, treatment guidance, patient management guidance or stratification will be displayed and/or printed for the user (typically a health professional such as a physician).

In one embodiment of the invention, a software system can be employed, in which a machine learning algorithm is evident, preferably to identify hospitalized patients that display symptoms of AP and either suffer from acute pancreatitis or not as determined by the method of the present invention using data from electronic health records (EHRs). A machine learning approach can be trained on a random forest classifier using EHR data (such as labs, biomarker expression, vitals, and demographics) from patients. Machine learning is a type of artificial intelligence that provides computers with the ability to learn complex patterns in data without being explicitly programmed, unlike simpler rule-based systems. Earlier studies have used electronic health record data to trigger alerts to detect clinical deterioration in general. In one embodiment of the invention the processing of GP2a levels may be incorporated into appropriate software for comparison to existing data sets, for example GP2a levels may also be processed in machine learning software to assist in diagnosing of acute pancreatitis or other pancreatic diseases.

In a preferred embodiment the kit according to the present invention comprises a computer software, which is configured for determining whether the GP2a concentration in said sample is above or below 0.7 ng/mL.

The embodiments described herein with reference to the kit of the present invention are intended to also relate to structural features of the components of the method as described herein. The features of the kit as described herein may therefore also be used to characterize the method, and vice versa.

In another preferred embodiment the kit according to the present invention comprises a computer software, which is configured for determining GP2a concentration in said sample using a threshold value of 0.7 ng/mL.

In another preferred embodiment the kit according to the present invention comprises a computer software, which is configured for determining GP2a concentration in said sample using a threshold region of 0.2-1.0 ng/mL, 0.3-1.0 ng/ml, 0.4-1.0 ng/ml, 0.5-1.0 ng/ml, 0.6-1.0 ng/ml, 0.7-1.0 ng/ml, 0.8-1.0 ng/ml, 0.9-1.0 ng/ml, 0.2-0.9 ng/ml, 0.2-0.8 ng/ml, 0.2 0.7 ng/ml, 0.2-0.6 ng/ml, 0.2-0.5 ng/ml, 0.2-0.4 ng/ml, or 0.2-0.3 ng/ml.

The invention further provides a system for the diagnosis of acute pancreatitis (AP) in a subject by detection of Glycoprotein 2 isoform alpha (GP2a) protein, comprising:

as components of a kit a) an affinity reagent directed against GP2a and a solid surface for immobilization of said affinity reagent, or an affinity reagent directed against GP2a immobilized to a solid surface, b) a labelled secondary affinity reagent directed to GP2 and means for detecting the signal emitted from said label, and c) computer software configured for determining the concentration of GP2a captured from a sample via an affinity reagent directed against GP2a, wherein said software is further configured for determining whether the GP2a concentration in said sample is greater than the average concentration of GP2a in one or more control samples, such as in a group of healthy individuals, and a computer system for automated analysis of one or more samples, comprising a computer processing device and a plate reader or camera device suitable for detecting the signal of the labeled secondary affinity reagent directed to GP2.

The combination of a kit according to the present invention with a computer system appropriate for carrying out automated analysis of one or more samples has been motivated only by the novel and surprising finding of the present invention. The combination of the components of the kit and the computer system therefore is to be considered an unexpected development of the art. There exists no suggestion in the relevant literature that the provision of a system comprising said components should have been developed.

It is a great advantage of the computer system for automated analysis of one or more samples that it comprises components that are available in most laboratories carrying out in vitro methods of serological diagnosis. The one skilled in the art knows different embodiments of computer processing devices, plate readers and camera devices for detecting the signal of the labeled secondary affinity reagent directed to GP2.

In one embodiment the invention additionally comprises a treatment of the subject after determining a concentration of GP2a in said sample. It is particularly advantageous that the present invention enables rapid diagnosis of acute pancreatitis in a patient and differentiation of acute pancreatitis from other pancreatic diseases in such a short time frame after occurrence of symptoms. This allows the initiation of a treatment or a treatment regime upon determining the concentration of GP2a in said sample. The treatment may be specific to acute pancreatitis and can therefore differ from a treatment regime that would be initiated in patients suffering from other pancreatic diseases such as chronic pancreatitis or pancreatic cancer. The treatment or treatment regime may be suggested or provided by the computer system of the present invention.

Treatment in the context of the present invention comprises, without limitation, fluid replacement, pain control, bowel rest, nutritional support, antibiotics, carbapenems such as imipenem or meropenem, pefloxacin, endoscopic retrograde cholangiopancreatography (ERCP), surgery such as minimally invasive management (necrosectomy through small incision in skin (left flank) or abdomen), conventional management (necrosectomy with simple drainage), closed management (necrosectomy with closed continuous postoperative lavage) and open management (necrosectomy with planned staged reoperations at definite intervals (up to 20+ reoperations in some cases)), pancreatic enzyme inhibitors, octreotide and combinations thereof.

DETAILED DESCRIPTION OF THE INVENTION

TABLE 1

Terminology of GP2 isoforms. Isoforms 1 and 2 may be referred to as isoform alpha.

| Amino acids | | Pubmed # |
|---|---|---|
| 537 | Isoform 1 SEQ ID NO. 1 | NP_001007241.2 |
| 534 | Isoform 2 SEQ ID NO. 2 | NP_001493.2 |
| 390 | Isoform 3 SEQ ID NO. 3 | NP_001007242.2 |
| 387 | Isoform 4 SEQ ID NO. 4 | NP_001007243.2 |

TABLE 2

Amino Acid sequences of isoforms 1 to 4

| SEQ ID NO. | Amino Acid Sequence | Description |
|---|---|---|
| SEQ ID NO 1 | MPHLMERMVGSGLLWLALVSC ILTQASAVQRGYGNPIEASSY GLDLDCGAPGTPEAHVCFDPC QNYTLLDEPFRSTENSAGSQG CDKNMSGWYRFVGEGGVRMSE TCVQVHRCQTDAPMWLNGTHP ALGDGITNHTACAHWSGNCCF WKTEVLVKACPGGYHVYRLEG TPWCNLRYCTVPRDPSTVEDK CEKACRPEEECLALNSTWGCF CRQDLNSSDVHSLQPQLDCGP REIKVKVDKCLLGGLGLGEEV IAYLRDPNCSSILQTEERNWV SVTSPVQASACRNILERNQTH AIYKNTLSLVNDFIIRDTILN INFQCAYPLDMKVSLQAALQP IVSSLNVSVDGNGEFIVRMAL FQDQNYTNPYEGDAVELSVES VLYVGAILEQGDTSRFNLVLR NCYATPTEDKADLVKYFIIRN SCSNQRDSTIHVEENGQSSES RFSVQMFMFAGHYDLVFLHCE IHLCDSLNEQCQPSCSRSQVR SEVPAIDLARVLDLGPITRRG AQSPGVMNGTPSTAGFLVAWP MVLLTVLLAWLF | Transcript Variant: This variant (1) represents the longest transcript, although it occurs rarely. It encodes the longest protein (isoform 1). |
| SEQ ID NO 2 | MPHLMERMVGSGLLWLALVSC ILTQASAVQRGYGNPIEASSY GLDLDCGAPGTPEAHVCFDPC QNYTLLDEPFRSTENSAGSQG CDKNMSGWYRFVGEGGVRMSE TCVQVHRCQTDAPMWLNGTHP ALGDGITNHTACAHWSGNCCF WKTEVLVKACPGGYHVYRLEG TPWCNLRYCTDPSTVEDKCEK ACRPEEECLALNSTWGCFCRQ DLNSSDVHSLQPQLDCGPREI KVKVDKCLLGGLGLGEEVIAY LRDPNCSSILQTEERNWVSVT SPVQASACRNILERNQTHAIY KNTLSLVNDFIIRDTILNINF QCAYPLDMKVSLQAALQPIVS SLNVSVDGNGEFIVRMALFQD QNYTNPYEGDAVELSVESVLY VGAILEQGDTSRFNLVLRNCY ATPTEDKADLVKYFIIRNSCS NQRDSTIHVEENGQSSESRFS VQMFMFAGHYDLVFLHCEIHL CDSLNEQCQPSCSRSQVRSEV PAIDLARVLDLGPITRRGAQS PGVMNGTPSTAGFLVAWPMVL LTVLLAWLF | Transcript Variant: This variant (2) lacks an alternate in-frame segment, compared to variant 1. The resulting protein (isoform 2) is shorter than isoform 1. Isoform 2 is also known as the alpha form. |
| SEQ ID NO 3 | MPHLMERMVGSGLLWLALVSC ILTQASAVQRVPRDPSTVEDK CEKACRPEEECLALNSTWGCF CRQDLNSSDVHSLQPQLDCGP REIKVKVDKCLLGGLGLGEEV IAYLRDPNCSSILQTEERNWV SVTSPVQASACRNILERNQTH AIYKNTLSLVNDFIIRDTILN INFQCAYPLDMKVSLQAALQP IVSSLNVSVDGNGEFIVRMAL FQDQNYTNPYEGDAVELSVES VLYVGAILEQGDTSRFNLVLR NCYATPTEDKADLVKYFIIRN SCSNQRDSTIHVEENGQSSES RFSVQMFMFAGHYDLVFLHCE IHLCDSLNEQCQPSCSRSQVR SEVPAIDLARVLDLGPITRRG AQSPGVMNGTPSTAGFLVAWP MVLLTVLLAWLF | Transcript Variant: This variant (3) lacks an alternate in-frame segment, compared to variant 1. The resulting protein (isoform 3) has a shorter N-terminus when compared to isoform 1 although the 31 most N-term aas are maintained. |
| SEQ ID NO 4 | MPHLMERMVGSGLLWLALVSC ILTQASAVQRDPSTVEDKCEK ACRPEEECLALNSTWGCFCRQ DLNSSDVHSLQPQLDCGPREI KVKVDKCLLGGLGLGEEVIAY LRDPNCSSILQTEERNWVSVT SPVQASACRNILERNQTHAIY KNTLSLVNDFIIRDTILNINF QCAYPLDMKVSLQAALQPIVS SLNVSVDGNGEFIVRMALFQD QNYTNPYEGDAVELSVESVLY VGAILEQGDTSRFNLVLRNCY ATPTEDKADLVKYFIIRNSCS NQRDSTIHVEENGQSSESRFS VQMFMFAGHYDLVFLHCEIHL CDSLNEQCQPSCSRSQVRSEV PAIDLARVLDLGPITRRGAQS PGVMNGTPSTAGFLVAWPMVL LTVLLAWLF | Transcript Variant: This variant (4) lacks two alternate in-frame segments, compared to variant 1. The resulting protein (isoform 4) has a shorter N-terminus when compared to isoform 1, although the 31 most N-term aas are maintained. Isoform 4 is also known as the beta form. |

TABLE 3

DNA-Sequences (such as cDNA) corresponding to each of the isoforms

| SEQ ID NO. | Nucleotide Sequence | Description |
|---|---|---|
| SEQ ID NO 5 | ATGCCTCACCTTATGGAAAGGATGGTGGGC TCTGGCCTCCTGTGGCTGGCCTTGGTCTCC TGCATTCTGACCCAGGCATCTGCAGTGCAG CGAGGTTATGGAAACCCCATTGAAGCCAGT TCGTATGGGCTGGACCTGGACTGCGGAGCT CCTGGCACCCCAGAGGCTCATGTCTGTTTT GACCCCTGTCAGAATTACACCCTCCTGGAT GAACCCTTCCGAAGCACAGAGAACTCAGCA GGGTCCCAGGGGTGCGATAAAAACATGAGC GGCTGGTACCGCTTTGTAGGGGAAGGAGGA GTAAGGATGTCGGAGACCTGTGTCCAGGTG CACCGATGCCAGACAGACGCTCCCATGTGG CTGAATGGGACCCACCCCTGCCCTTGGGAT GGCATCACCAACCACACTGCCTGTGCCCAT TGGAGTGGCAACTGCTGTTTCTGGAAAACA GAGGTGCTGGTGAAGGCCTGCCCAGGCGGG TACCATGTGTACCGGTTGGAAGGCACTCCC TGGTGTAATCTGAGATACTGCACAGTTCCA CGAGACCCATCCACTGTGGAGGACAAGTGT GAGAAGGCCTGCCGCCCCGAGGAGGAGTGC CTTGCCCTCAACAGCACCTGGGGCTGTTTC TGCAGACAGGACCTCAATAGTTCTGATGTC CACAGTTTGCAGCCTCAGCTAGACTGTGGG CCCAGGGAGATCAAGGTGAAGGTGGACAAA TGTTTGCTGGGAGGCCTGGGTTTGGGGGAG GAGGTCATTGCCTACCTGCGAGACCCAAAC TGCAGCAGCATCTTGCAGACAGAGGAGAGG AACTGGGTATCTGTGACCAGCCCCGTCCAG GCTAGTGCCTGCAGGAACATTCTGGAGAGA AATCAAACCCATGCCATCTACAAAAACACC CTCTCCTTGGTCAATGATTTCATCATCAGA GACACCATCCTCAACATCAACTTCCAATGT GCCTACCCACTGGACATGAAAGTCAGCCTC CAAGCTGCCTTGCAGCCCATTGTAAGTTCC CTGAACGTCAGTGTGGACGGGAATGGAGAG TTCATTGTCAGGATGGCCCTCTTCCAAGAC CAGAACTACACGAATCCTTACGAAGGGGAT GCAGTTGAACTGTCTGTTGAGTCCGTGCTG TATGTGGGTGCCATCTTGGAACAAGGGGAC ACCTCCCGGTTTAACCTGGTGTTGAGGAAC TGCTATGCCACCCCCACTGAAGACAAGGCT GACCTTGTGAAGTATTTCATCATCAGAAAC AGCTGCTCAAATCAACGTGATTCCACCATC | Isoform 1 CCDS Database CCDS42128.1 |

TABLE 3-continued

DNA-Sequences (such as cDNA) corresponding to each of the isoforms

| SEQ ID NO. | Nucleotide Sequence | Description |
|---|---|---|
| | CACGTGGAGGAGAATGGGCAGTCCTCGGAA<br>AGCCGGTTCTCAGTTCAGATGTTCATGTTT<br>GCTGGACATTATGACCTAGTTTTCCTGCAT<br>TGTGAGATTCATCTCTGTGATTCTCTTAAT<br>GAACAGTGCCAGCCTTCTTGCTCAAGAAGT<br>CAAGTCCGCAGTGAAGTACCGGCCATCGAC<br>CTAGCCCGGGTTCTAGATTTGGGGCCCATC<br>ACTCGGAGAGGTGCACAGTCTCCCGGTGTC<br>ATGAATGGAACCCCTAGCACTGCAGGGTTC<br>CTGGTGGCCTGGCCTATGGTCCTCCTGACT<br>GTCCTCCTGGCTTGGCTGTTCTGA | |
| SEQ ID NO 6 | ATGCCTCACCTTATGGAAAGGATGGTGGGC<br>TCTGGCCTCCTGTGGCTGGCCTTGGTCTCC<br>TGCATTCTGACCCAGGCATCTGCAGTGCAG<br>CGAGGTTATGAAACCCCATTGAAGCCAGT<br>TCGTATGGGCTGGACCTGGACTGCGGAGCT<br>CCTGGCACCCCAGAGGCTCATGTCTGTTTT<br>GACCCCTGTCAGAATTACACCCTCCTGGAT<br>GAACCCTTCCGAAGCACAGAGAACTCAGCA<br>GGGTCCCAGGGGTGCGATAAAAACATGAGC<br>GGCTGGTACCGCTTTGTAGGGGAAGGAGGA<br>GTAAGGATGTCGGAGACCTGTGTCCAGGTG<br>CACCGATGCCAGACAGACGCTCCCATGTGG<br>CTGAATGGGACCCACCCTGCCCTTGGGGAT<br>GGCATCACCAACCACACTGCCTGTGCCCAT<br>TGGAGTGGCAACTGCTGTTTCTGGAAAACA<br>GAGGTGCTGGTGAAGGCCTGCCCAGGCGGG<br>TACCATGTGTACCGGTTGGAAGGCACTCCC<br>TGGTGTAATCTGAGATACTGCACAGACCCA<br>TCCACTGTGGAGGACAAGTGTGAGAAGGCC<br>TGCCGCCCCGAGGAGGAGTGCCTTGCCCTC<br>AACAGCACCTGGGGCTGTTTCTGCAGACAG<br>GACCTCAATAGTTCTGATGTCCACAGTTTG<br>CAGCCTCAGCTAGACTGTGGGCCCAGGGAG<br>ATCAAGGTGAAGGTGGACAAATGTTTGCTG<br>GGAGGCCTGGGTTTGGGGGAGGAGGTCATT<br>GCCTACCTGCGAGACCCAAACTGCAGCAGC<br>ATCTTGCAGACAGAGGAGAGGAACTGGGTA<br>TCTGTGACCAGCCCCGTCCAGGCTAGTGCC<br>TGCAGGAACATTCTGGAGAGAAATCAAACC<br>CATGCCATCTACAAAAACACCCTCTCCTTG<br>GTCAATGATTTCATCATCAGAGACACCATC<br>CTCAACATCAACTTCCAATGTGCCTACCCA<br>CTGGACATGAAAGTCAGCCTCCAAGCTGCC<br>TTGCAGCCCATTGTAAGTTCCCTGAACGTC<br>AGTGTGGACGGGAATGGAGAGTTCATTGTC<br>AGGATGGCCCTCTTCCAAGACCAGAACTAC<br>ACGAATCCTTACGAAGGGGATGCAGTTGAA<br>CTGTCTGTTGAGTCCGTGCTGTATGTGGGT<br>GCCATCTTGGAACAAGGGGACACCTCCCGG<br>TTTAACCTGGTGTTGAGGAACTGCTATGCC<br>ACCCCCACTGAAGACAAGGCTGACCTTGTG<br>AAGTATTTCATCATCAGAAACAGCTGCTCA<br>AATCAACGTGATTCCACCATCCACGTGGAG<br>GAGAATGGGCAGTCCTCGGAAAGCCGGTTC<br>TCAGTTCAGATGTTCATGTTTGCTGGACAT<br>TATGACCTAGTTTTCCTGCATTGTGAGATT<br>CATCTCTGTGATTCTCTTAATGAACAGTGC<br>CAGCCTTCTTGCTCAAGAAGTCAAGTCCGC<br>AGTGAAGTACCGGCCATCGACCTAGCCCGG<br>GTTCTAGATTTGGGGCCCATCACTCGGAGA<br>GGTGCACAGTCTCCCGGTGTCATGAATGGA<br>ACCCCTAGCACTGCAGGGTTCCTGGTGGCC<br>TGGCCTATGGTCCTCCTGACTGTCCTCCTG<br>GCTTGGCTGTTCTGA | Isoform 2<br>CCDS<br>Database<br>CCDS10582.2 |
| SEQ ID NO 7 | ATGCCTCACCTTATGGAAAGGATGGTGGGC<br>TCTGGCCTCCTGTGGCTGGCCTTGGTCTCC<br>TGCATTCTGACCCAGGCATCTGCAGTGCAG<br>CGAGTTCCACGAGACCCATCCACTGTGGAG<br>GACAAGTGTGAGAAGGCCTGCCGCCCCGAG<br>GAGGAGTGCCTTGCCCTCAACAGCACCTGG<br>GGCTGTTTCTGCAGACAGGACCTCAATAGT | Isoform 3<br>CCDS<br>Database<br>CCDS45433.1 |

TABLE 3-continued

DNA-Sequences (such as cDNA) corresponding to each of the isoforms

| SEQ ID NO. | Nucleotide Sequence | Description |
|---|---|---|
| | TCTGATGTCCACAGTTTGCAGCCTCAGCTA<br>GACTGTGGGCCCAGGGAGATCAAGGTGAAG<br>GTGGACAAATGTTTGCTGGGAGGCCTGGGT<br>TTGGGGGAGGAGGTCATTGCCTACCTGCGA<br>GACCCAAACTGCAGCAGCATCTTGCAGACA<br>GAGGAGGAACTGGGTATCTGTGACCAGC<br>CCCGTCCAGGCTAGTGCCTGCAGGAACATT<br>CTGGAGAGAAATCAAACCCATGCCATCTAC<br>AAAAACACCCTCTCCTTGGTCAATGATTTC<br>ATCATCAGAGACACCATCCTCAACATCAAC<br>TTCCAATGTGCCTACCCACTGGACATGAAA<br>GTCAGCCTCCAAGCTGCCTTGCAGCCCATT<br>GTAAGTTCCCTGAACGTCAGTGTGGACGGG<br>AATGGAGAGTTCATTGTCAGGATGGCCCTC<br>TTCCAAGACCAGAACTACACGAATCCTTAC<br>GAAGGGGATGCAGTTGAACTGTCTGTTGAG<br>TCCGTGCTGTATGTGGGTGCCATCTTGGAA<br>CAAGGGGACACCTCCCGGTTTAACCTGGTG<br>TTGAGGAACTGCTATGCCACCCCCACTGAA<br>GACAAGGCTGACCTTGTGAAGTATTTCATC<br>ATCAGAAACAGCTGCTCAAATCAACGTGAT<br>TCCACCATCCACGTGGAGGAGAATGGGCAG<br>TCCTCGGAAAGCCGGTTCTCAGTTCAGATG<br>TTCATGTTTGCTGGACATTATGACCTAGTT<br>TTCCTGCATTGTGAGATTCATCTCTGTGAT<br>TCTCTTAATGAACAGTGCCAGCCTTCTTGC<br>TCAAGAAGTCAAGTCCGCAGTGAAGTACCG<br>GCCATCGACCTAGCCCGGGTTCTAGATTTG<br>GGGCCCATCACTCGGAGAGGTGCACAGTCT<br>CCCGGTGTCATGAATGGAACCCCTAGCACT<br>GCAGGGTTCCTGGTGGCCTGGCCTATGGTC<br>CTCCTGACTGTCCTCCTGGCTTGGCTGTTC<br>TGA | |
| SEQ ID NO 8 | ATGCCTCACCTTATGGAAAGGATGGTGGGC<br>TCTGGCCTCCTGTGGCTGGCCTTGGTCTCC<br>TGCATTCTGACCCAGGCATCTGCAGTGCAG<br>CGAGACCCATCCACTGTGGAGGACAAGTGT<br>GAGAAGGCCTGCCGCCCCGAGGAGGAGTGC<br>CTTGCCCTCAACAGCACCTGGGGCTGTTTC<br>TGCAGACAGGACCTCAATAGTTCTGATGTC<br>CACAGTTTGCAGCCTCAGCTAGACTGTGGG<br>CCCAGGGAGATCAAGGTGAAGGTGGACAAA<br>TGTTTGCTGGGAGGCCTGGGTTTGGGGGAG<br>GAGGTCATTGCCTACCTGCGAGACCCAAAC<br>TGCAGCAGCATCTTGCAGACAGAGGAGAGG<br>AACTGGGTATCTGTGACCAGCCCCGTCCAG<br>GCTAGTGCCTGCAGGAACATTCTGGAGAGA<br>AATCAAACCCATGCCATCTACAAAAACACC<br>CTCTCCTTGGTCAATGATTTCATCATCAGA<br>GACACCATCCTCAACATCAACTTCCAATGT<br>GCCTACCCACTGGACATGAAAGTCAGCCTC<br>CAAGCTGCCTTGCAGCCCATTGTAAGTTCC<br>CTGAACGTCAGTGTGGACGGGAATGGAGAG<br>TTCATTGTCAGGATGGCCCTCTTCCAAGAC<br>CAGAACTACACGAATCCTTACGAAGGGGAT<br>GCAGTTGAACTGTCTGTTGAGTCCGTGCTG<br>TATGTGGGTGCCATCTTGGAACAAGGGGAC<br>ACCTCCCGGTTTAACCTGGTGTTGAGGAAC<br>TGCTATGCCACCCCCACTGAAGACAAGGCT<br>GACCTTGTGAAGTATTTCATCATCAGAAAC<br>AGCTGCTCAAATCAACGTGATTCCACCATC<br>CACGTGGAGGAGAATGGGCAGTCCTCGGAA<br>AGCCGGTTCTCAGTTCAGATGTTCATGTTT<br>GCTGGACATTATGACCTAGTTTTCCTGCAT<br>TGTGAGATTCATCTCTGTGATTCTCTTAAT<br>GAACAGTGCCAGCCTTCTTGCTCAAGAAGT<br>CAAGTCCGCAGTGAAGTACCGGCCATCGAC<br>CTAGCCCGGGTTCTAGATTTGGGGCCCATC<br>ACTCGGAGAGGTGCACAGTCTCCCGGTGTC<br>ATGAATGGAACCCCTAGCACTGCAGGGTTC<br>CTGGTGGCCTGGCCTATGGTCCTCCTGACT<br>GTCCTCCTGGCTTGGCTGTTCTGA | Isoform 4<br>CCDS<br>Database<br>CCD545432.1 |

The CCDS reference refers to the CCDS project as described in "The consensus coding sequence (CCDS) project: Identifying a common protein-coding gene set for the human and mouse genomes", Pruitt K D, et al, Genome Res. 2009 July; 19(7):1316-23.

The term "in vitro method" relates to a method that is performed on a sample, for example, without limitation, a tissue or a bodily fluid, outside of the outside their normal biological context.

The term "sample" includes any biological specimen obtained from an individual. Suitable samples for use in the present invention include, without limitation, whole blood, plasma, serum, saliva, urine, stool, tears, any other bodily fluid, pure pancreatic juices or duodenal juices, tissue samples (e.g., biopsy) and cellular extracts thereof (e.g., red blood cellular extract). In a preferred embodiment, the sample is a serum sample. The use of samples such as serum, saliva, and urine is well known in the art (see, e.g., Hashida et al., J. Clin. Lab. Anal., 11:267-86 (1997)). One skilled in the art will appreciate that samples such as serum samples can be diluted prior to analysis.

The term "individual," "subject," or "patient" typically refers to humans, but also to other animals including, e.g., other primates, rodents, canines, felines, equines, ovines, porcines, and the like.

As used herein, the term "substantially the same amino acid sequence" includes an amino acid sequence that is similar, but not identical to, the naturally-occurring amino acid sequence. For example, an amino acid sequence, i.e., polypeptide, that has substantially the same amino acid sequence as the GP2 isoforms in SEQ ID NO 1 to 4 and can have one or more modifications such as amino acid additions, deletions, or substitutions relative to the amino acid sequence of the GP2 isoforms, provided that the modified polypeptide retains substantially at least one biological activity of GP2 such as immunoreactivity, in particular the immune reactivity specific to the diseases capable of being diagnosed according to the present invention. A particularly useful modification of a polypeptide of the present invention, or a fragment thereof, is a modification that confers, for example, increased stability or reactivity. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

As used herein, the term "GP2 isoform" includes a protein that has at least about 50% amino acid identity with one or more SEQ ID No 1 to 4. As a non-limiting example, an GP2 isoform of the invention can have at least about 60%, 65%, 70%, 75%, 80%, 85%, 90%, 91%, 92%, 93%, 94%, 95%, 96%, 97%, 98%, or 99% amino acid sequence identity with one or more SEQ ID No 1 to 4. Nucleic acid variants to SEQ ID NO 5 to 8 are also encompassed herein that encode a protein sequence of SEQ ID NO 1 to 4, or a sequence with substantially the same amino acid sequence. The complementary nucleic acid sequence is also encompassed, as is a degenerate sequence modified to use the degenerate nature of the genetic code, as is known to a skilled person.

The amino acid sequences may also comprise 0 to 100, 2 to 50, 5 to 20, or for example 8 to 15, or any value from 0 to 20, amino acid additions or deletions at either the N- and/or C-terminus of the proteins. The termini may also be modified with additional linker sequences, or removal of sequences, as long as the antibody binding properties and immunoreactivity of the protein is essentially maintained and the antibodies as described herein bind in an analogous manner to the specific sequence provided.

Various ways of preparing functionally analogous peptides have been disclosed in the prior art. Peptides designed starting from the peptides of the invention using such methods are included in the teaching according to the invention. For example, one way of generating functionally analogous peptides has been described in PNAS USA 1998, Oct. 13, 9521, 12179-84; WO 99/6293 and/or WO 02/38592; the above teachings are hereby incorporated in the disclosure of the invention. That is, all peptides, peptide fragments or structures comprising peptides generated using the methods mentioned above—starting from the peptides of the invention—are peptides according to the invention, provided they accomplish the object of the invention and, in particular, interact with the specific antibodies.

Affinity reagents, such as antibodies, directed against GP2 isoforms or GP2 proteins with substantially the same amino acid sequence may therefore be employed in the present invention in order to detect GP2a.

The GP2 isoforms may also be described as antigens, as they react with an antibody targeted to said GP2 isoform protein. The GP2 isoforms may also be referred to as proteins or targets.

The terms "diagnosis" and "diagnosing" include the use of the devices, methods, and systems, of the present invention to determine the presence or absence or likelihood of presence or absence of a medically relevant disorder in an individual. The term also includes devices, methods, and systems for assessing the level of disease activity in an individual. In some embodiments, statistical algorithms are used to diagnose a mild, moderate, severe, or fulminant form of the disorder based upon the criteria developed by Truelove et al., Br. Med. J., 12:1041-1048 (1955). In other embodiments, statistical algorithms are used to diagnose a mild to moderate, moderate to severe, or severe to fulminant form of the IBD based upon the criteria developed by Hanauer et al., Am. J. Gastroenterol., 92:559-566 (1997). In other embodiments, the presence of GP2 antibodies is used to diagnose Crohn's disease. One skilled in the art will know of other methods for evaluating the severity of IBD in an individual.

The analysis described herein of determining GP2 concentration via antibody binding to one or more GP2 isoforms is a preferred method of the present invention. For this embodiment the amount of antibodies specific to certain GP2 isoforms provided for the experiment should be controlled carefully to enable direct comparative analysis. Alternatively, or in combination, control values or standards may be used that provide samples with GP2 isoforms or represent control amounts thereof, as have already been obtained from previous analytical tests. It is possible to use control values having been generated by the testing of cohorts or other large numbers of subjects suffering from any given disease or control group. Appropriate statistical means are known to those skilled in the art for analysis and comparison of such data sets. Control samples for positive controls (such as disease sufferers) or negative controls (from healthy subjects) may be used for reference values in either simultaneous of non-simultaneous comparison.

The term "pancreatic diseases" refers to diseases of the pancreas, including, without limitation, acute pancreatitis, chronic pancreatitis, diabetes mellitus (type 1 and type 2), exocrine pancreatic insufficiency, cystic fibrosis, pancreatic pseudocysts, cysts of the pancreas, congenital malformations of the pancreas, pancreas divisum, annular pancreas, pancreatic tumors (benign and malignant), pancreatic cancer, serous cystadenoma of the pancreas, solid pseudopapillary neoplasm, hemosuccus pancreaticus.

Diseases affecting the pancreas include all kinds of diseases that affect the pancreas and cause symptoms similar to the symptoms of pancreatic diseases. Diseases affecting the pancreas, include, without limitation, gastrointestinal cancer, liver cancer, neuroendocrine tumor, sarcoma, peptic ulcer, peritonitis, inflammatory bowl disease, ulcerative colitis, gastritis.

In one embodiment the assay described herein is capable of differentiating acute pancreatitis from other pancreatic diseases.

"Pancreatitis" in the meaning of the invention is inflammation of the pancreas which can be acute or take a chronic course. Pancreatitis is usually induced by activation of pancreatic enzymes within the organ. The function of these enzymes is to digest proteins and fat so that autodigestion of the organ is induced. Autodigestion results in inflammation of the pancreas. In severe cases, hemorrhage, serious tissue damage, infections and cysts may develop. An inflamed gland may cause enzymes to enter the bloodstream, thus reaching the lungs, heart and kidneys where further damage may arise. "Acute pancreatitis" develops when the pancreas suddenly becomes inflamed but recovers afterwards. Some patients suffer from acute pancreatitis a number of times but recover completely each time. Acute pancreatitis appears suddenly and can be a serious, life-threatening disease causing a large number of complications, but the patients normally recover from acute pancreatitis. The incidence is about five to ten new diseases per 100,000 inhabitants per year.

"Chronic pancreatitis" is a long-standing inflammation of the pancreas that alters the organ's normal structure and functions. It can present as episodes of acute inflammation in a previously injured pancreas, or as chronic damage with persistent pain or malabsorption. It is a disease process characterized by irreversible damage to the pancreas as distinct from reversible changes in acute pancreatitis.

"Symptoms of having AP" are essentially the same as the symptoms of other pancreatic disease and include, without limitation, upper abdominal pain, abdominal pain that radiates to the back, abdominal pain that feels worse after eating, nausea, vomiting, tenderness when touching the abdomen, upper abdominal pain, losing weight without trying, oily and smelly stools (steatorrhea). Such symptoms are well-known to skilled practitioners in the field.

The term "affinity reagent" in the context of the present invention relates to an antibody, peptide, nucleic acid, small molecule, or any other molecule that specifically binds to a target molecule in order to identify, track, capture, or influence its activity. The term "capturing" refers to binding of a target molecule by an affinity reagent.

The term "secondary affinity reagent" refers to any affinity reagent according to the above definition, which is used to bind to an antigen that is already bound by another affinity reagent.

As used herein, the term "antibody" includes a population of immunoglobulin molecules, which can be polyclonal or monoclonal and of any isotype, or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')2 is included within the meaning of the term antibody.

The term "monoclonal antibody" refers to antibodies that are made by identical immune cells that are all clones of a unique parent cell, in contrast to polyclonal antibodies, which are made from several different immune cells. Monoclonal antibodies can have monovalent affinity, in that they bind to the same epitope (the part of an antigen that is recognized by the antibody). Engineered bispecific monoclonal antibodies also exist, where each "arm" of the antibody is specific for a different epitope. Given almost any substance, it is possible to produce monoclonal antibodies that specifically bind to that substance; they can then serve to detect or purify that substance.

In another advantageous embodiment an immunoassay is used in the detection of GP2a to which end binding of the GP2a specific antibody to a solid phase is envisaged. Following addition of sample solution, the patient's GP2a included therein binds to the GP2a antibody. GP2a, which is obtained e.g. from the serum or stool of a patient and bound to the GP2a antibody, is subsequently detected using a label, or labelled reagent and optionally quantified.

Thus, according to the invention, detection of GP2a in this method is effected using labelled reagents according to the well-known ELISA (Enzyme-Linked Immunosorbent Assay) technology. Labels according to the invention therefore comprise enzymes catalyzing a chemical reaction which can be determined by optical means, especially by means of chromogenic substrates, chemiluminescent methods or fluorescent dyes. In another preferred embodiment GP2a is detected by labelling with weakly radioactive substances in radioimmunoassays (RIA) wherein the resulting radioactivity is measured.

As examples of means for detecting the label in the method of the present invention, a variety of immunoassay techniques, including competitive and non-competitive immunoassays, can be used to determine the presence or level of one or more markers in a sample (see, e.g., Self et al., Curr. Opin. Biotechnol., 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); lateral flow tests; and chemiluminescence assays (CL).

In another preferred embodiment of the method according to the invention GP2a is detected in a lateral flow test, which can also be referred to as immunochromatographic test or lateral flow immunochromatographic test. Lateral flow tests are preferably based on a series of capillary beds, such as, for example, pieces of porous paper, microstructured polymer, or sintered polymer. Each of these elements has the capacity to transport fluid spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes colour. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the wick that simply acts as a waste container. Lateral Flow Tests can operate as either competitive or sandwich assays and can in principle be performed by using any coloured particle. However latex (blue colour) or nanometer sized particles of gold (red colour) are commonly used. The gold particles are red in colour due to localised surface plasmon resonance. Fluorescent or magnetic labelled particles can also be used, however these require the use of an electronic reader to assess the test result.

If desired, such immunoassays can be automated. Immunoassays can also be used in conjunction with laser induced fluorescence (see, e.g., Schmalzing et al., Electrophoresis, 18:2184-2193 (1997); Bao, J. Chromatogr. B. Biomed. Sci., 699:463-480 (1997)). Liposome immunoassays, such as flow-injection liposome immunoassays and liposome immunosensors, are also suitable for use in the present invention (see, e.g., Rongen et al., J. Immunol. Methods, 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., J. Clin. Chem. Clin. Biol. Chem., 27:261-276 (1989)).

In another preferred embodiment of the method according to the invention GP2a is detected in an immunoassay, preferably with direct or indirect coupling of one reactant to a labelling substance. This enables flexible adaptation of the method to the potentials and requirements of different laboratories and their laboratory diagnostic equipment. In one advantageous embodiment GP2a is detected in an immunoassay wherein GP2a is present dissolved in a liquid phase, preferably diluted in a conventional buffer solution well-known to those skilled in the art or in an undiluted body fluid. According to the invention, detection can also be effected using stool samples.

In another preferred embodiment of the invention, soluble or solid phase-bound antibodies are used to bind specific isoforms of GP2. In a second reaction step, secondary anti-GP2 affinity reagents are employed, preferably secondary anti-GP2 antibodies, which are detectably labelled conjugates of two components which can be conjugated with any conventional labelling enzymes, especially chromogenic and/or chemiluminescent substrates, preferably with horseradish peroxidase, alkaline phosphatase. The advantage of this embodiment lies in the use of ELISA technology usually available in laboratory facilities so that detection according to the invention can be established in a cost-effective manner. In another preferred embodiment of the invention secondary anti-GP2 affinity reagents is detectably coupled to fluorescein isothiocyanate (FITC). Much like the above-mentioned ELISA, the FITC technology represents a system that is available in many places and therefore allows smooth and low-cost establishment of the inventive detection in laboratory routine.

The term "denaturated" sample conditions" refers to conditions, which induce denaturation of the molecules contained in a sample. Denaturation is a process in which proteins or nucleic acids lose the quaternary structure, tertiary structure and secondary structure, which is present in their native state, by application of some external stress or compound such as a strong acid or base, a concentrated inorganic salt, an organic solvent (e.g., alcohol or chloroform), radiation or heat.

The term "serological diagnosis" refers to diagnostic tests or methods, which examine serum, bodily fluids or other biological samples for the presence of certain components through laboratory examination of antigen-antibody reactions in the serum. Serological techniques used for the analysis include, without limitation, ELISA, agglutination, precipitation, complement-fixation, and fluorescent antibodies.

A "kit for diagnosis" includes all necessary analyte specific reagents required for carrying out a diagnostic test. It may also contain instructions on how to conduct the test using the provided reagents.

Specific immunological binding of an affinity reagent such as an antibody to the marker of interest can be detected directly or indirectly via a label that is emitting a signal. Any given means for detecting these labels may be considered means for detecting the label according to the method of the invention. Direct labels include fluorescent or luminescent tags, metals, dyes, radionuclides, and the like, attached to the antibody. An antibody labeled with iodine-125 (125I) can be used for determining the levels of one or more markers in a sample. A chemiluminescence assay using a chemiluminescent antibody specific for the marker is suitable for sensitive, non-radioactive detection of marker levels. An antibody labeled with fluorochrome is also suitable for determining the levels of one or more markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')2 anti-human IgG-FITC is available from Tago Immunologicals (Burlingame, Calif.).

Indirect labels include various enzymes well-known in the art, such as horseradish peroxidase (HRP), alkaline phosphatase (AP), R-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm.

Methods for determining the concentration of specific molecules of interest in a sample a known to the person skilled in the art. For example, the concentration of the molecule of interest, for example a specific isoform of GP2, in a sample is determined by comparing the signal generated by a secondary affinity reagent according to the present invention that has captured the molecule of interest in said sample to the signal generated by a secondary affinity reagent that has captured the molecule of interest in a control sample, wherein the concentration of the molecule of interest in said control sample is known.

The method as described herein may also be described in terms of determining the amount of GP2, as an alternative or supplementary description to determining the concentration of GP2.

"Plate readers", also known as microplate readers or microplate photometers, are instruments which are used to detect biological, chemical or physical events of samples in microtiter plates. They are widely used in research, drug discovery, bioassay validation, quality control and manufacturing processes in the pharmaceutical and biotechnological industry and academic organizations. Sample reactions can be assayed, for example, without limitation, in 6-1536 well format microtiter plates. Common detection modes for microplate assays are, for example, without limitation, absorbance, fluorescence intensity, luminescence, time-resolved fluorescence, and fluorescence polarization.

A "camera device" in the context of the present invention is a device suitable for detection of the signal of the labeled secondary affinity reagent directed against GP2. The camera device can provided as being comprised in the plate reader or individually. The person skilled in the art is familiar with such devices, which are selected based on the label of the secondary affinity reagent.

A signal from the direct or indirect label can be analyzed, for example, using a spectrophotometer to detect colour from a chromogenic substrate; a radiation counter to detect radiation such as a gamma counter for detection of 125I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The invention also relates to protein and nucleic acid molecules corresponding to the sequences described herein, for example proteins or nucleic acid molecules comprising or consisting of said sequences.

As used herein, the term "GP2 isoform", "GP2", "GP2-antigen", "GP2-molecule", "GP2-protein", "GP2-peptide" or "GP2-autoantigen", or other GP2-referencing phrase relates to the novel GP2-isoforms of the sequences as disclosed herein, or functionally analogous sequences thereof, preferably to those isoforms 1, 2, 3 and 4. In a preferred embodiment of the method according to the invention the GP2-isoform is of human, animal, recombinant or synthetic origin. GP2 represents a highly conserved peptide so that GP2 of any origin can advantageously be used for detection as long as the sequence is functionally analog to the sequence according to the invention.

In another preferred embodiment of the invention the anti-GP2 antibody directed to GP2 in accordance with one or more of the sequences disclosed herein is bound to a solid phase. Binding of the anti-GP2 antibody in accordance with one or more of the sequences disclosed herein to the solid phase can be effected via a spacer. All those chemical compounds having suitable structural and functional preconditions for spacer function can be used as spacers as long as they do not modify the binding behaviour in such a way that binding of the anti-GP2 antibody to GP2 in accordance with one or more of the sequences disclosed herein is adversely affected.

In another preferred embodiment of the invention the affinity reagents according to the present application are immobilized. More specifically, the solid phase-bound anti-GP2, preferably anti-GP2a, antibody directed to a GP2 molecule in accordance with one or more of the sequences as disclosed herein is bound to organic, inorganic, synthetic and/or mixed polymers, preferably agarose, cellulose, silica gel, polyamides and/or polyvinyl alcohols. In the meaning of the invention, immobilization is understood to involve various methods and techniques to fix the peptides on specific carriers, e.g. according to WO 99/56126 or WO 02/26292. For example, immobilization can serve to stabilize the peptides so that their activity would not be reduced or adversely modified by biological, chemical or physical exposure, especially during storage or in single-batch use. Immobilization of the peptides allows repeated use under technical or clinical routine conditions; furthermore, a sample—preferably blood components—can be reacted with at least one of the peptides according to the invention in a continuous fashion. In particular, this can be achieved by means of various immobilization techniques, with binding of the peptides to other peptides or molecules or to a carrier proceeding in such a way that the three-dimensional structure—particularly in the active center mediating the interaction with the binding partner—of the corresponding molecules, especially of said peptides, would not be changed. Advantageously, there is no loss in specificity to the GP2a antibodies as a result of such immobilization. In the meaning of the invention, three basic methods can be used for immobilization:

(i) Crosslinking: in crosslinking, the peptides are fixed to one another without adversely affecting their activity. Advantageously, they are no longer soluble as a result of such crosslinking.

(ii) Binding to a carrier: binding to a carrier proceeds via adsorption, ionic binding or covalent binding, for example. Such binding may also take place inside microbial cells or liposomes or other membranous, closed or open structures. Advantageously, the peptides are not adversely affected by such fixing. For example, multiple or continuous use of carrier-bound peptides is possible with advantage in clinical diagnosis or therapy.

(iii) Inclusion: inclusion in the meaning of the invention especially proceeds in a semipermeable membrane in the form of gels, fibrils or fibers. Advantageously, encapsulated peptides are separated from the surrounding sample solution by a semipermeable membrane in such a way that interaction with the binding partner or fragments thereof still is possible. Various methods are available for immobilization, such as adsorption on an inert or electrically charged inorganic or organic carrier. For example, such carriers can be porous gels, aluminum oxide, bentonite, agarose, starch, nylon or polyacrylamide. Immobilization proceeds via physical binding forces, frequently involving hydrophobic interactions and ionic binding. Advantageously, such methods are easy to handle and have little influence on the conformation of the peptides. Advantageously, binding can be improved as a result of electrostatic binding forces between the charged groups of the peptides and the carrier, e.g. by using ion exchangers, particularly Sephadex.

Another method is covalent binding to carrier materials. In addition, the carriers may have reactive groups forming homopolar bonds with amino acid side chains. Suitable groups in peptides are carboxy, hydroxy and sulfide groups and especially the terminal amino groups of lysines. Aromatic groups offer the possibility of diazo coupling. The surface of microscopic porous glass particles can be activated by treatment with silanes and subsequently reacted with peptides. For example, hydroxy groups of natural polymers can be activated with bromocyanogen and subsequently coupled with peptides. Advantageously, a large number of peptides can undergo direct covalent binding with polyacrylamide resins. Inclusion in three-dimensional networks involves inclusion of the peptides in ionotropic gels or other structures well-known to those skilled in the art. More specifically, the pores of the matrix are such in nature that the peptides are retained, allowing interaction with the target molecules. In crosslinking, the peptides are converted into polymer aggregates by crosslinking with bifunctional agents. Such structures are gelatinous, easily deformable and, in particular, suitable for use in various reactors. By adding other inactive components such as gelatin in crosslinking, advantageous improvement of mechanical and binding properties is possible. In microencapsulation, the reaction volume of the peptides is restricted by means of membranes. For example, microencapsulation can be carried out in the form of an interfacial polymerization. Owing to the immobilization during microencapsulation, the peptides are made insoluble and thus reusable. In the meaning of the invention, immobilized peptides are all those peptides being in a condition that allows reuse thereof. Restricting the mobility and solubility of the antibodies by chemical, biological or physical means advantageously results in lower process cost.

The invention also relates to a diagnostic kit. The diagnostic kit optionally includes instructions concerning combining the contents of the kit for the detection of AP and differentiation from other diseases. For example, the instruction can be in the form of an instruction leaflet or other medium providing the user with information as to the type of method wherein the substances mentioned are to be used. Obviously, the information need not necessarily be in the form of an instruction leaflet, and the information may also be imparted via the Internet, for example.

FIGURES

The invention is further described by the following figures. These are not intended to limit the scope of the invention, but represent preferred embodiments of aspects of the invention provided for greater illustration of the invention described herein. The invention will be explained in more detail with reference to the figures.

Figure 1:
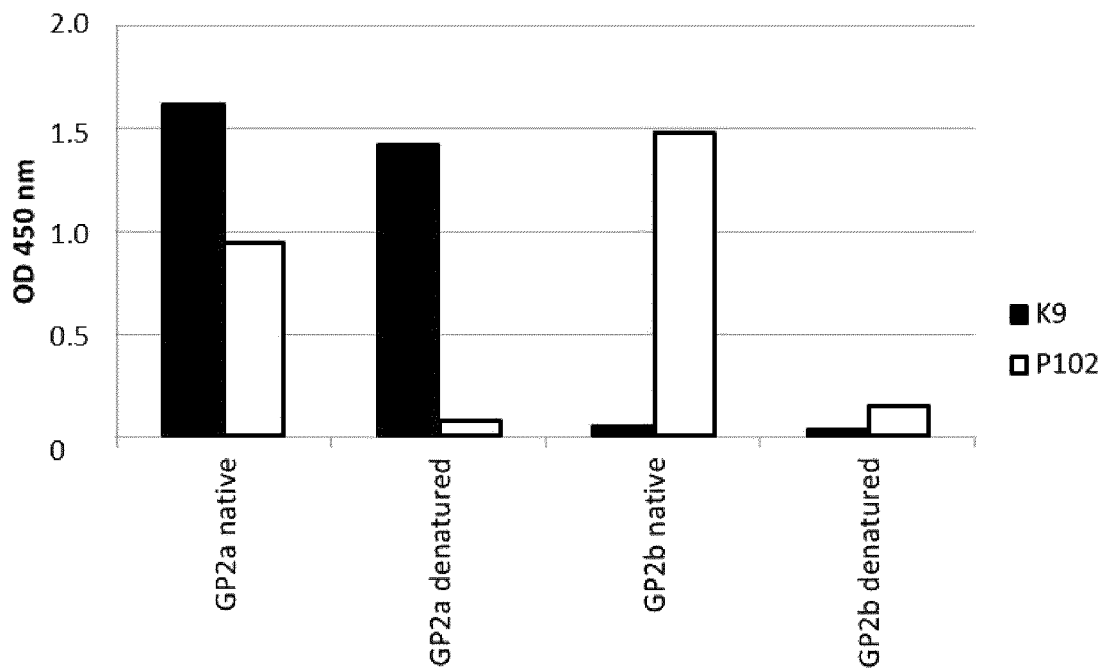
FIG. 1.

Solid phase ELISA analysis of recognition of soluble recombinant isoforms of GP2 (GP2a and GP2b) in their native (A) and denatured (B) state using different monoclonal antibodies, which have been generated against GP2. The respective monoclonal antibodies were used as solid phase immobilized antibodies in ELISA.

FIG. 2:

Correlation of glycoprotein 2 isoform a (GP2a) and total GP2 (GP2t). Serum GP2a and GP2t levels were detected in 153 patients with acute pancreatitis (AP) and 752 controls by enzyme-linked immunosorbent assay. The regression equation of all 905 samples was y=−0.05+0.41x, coefficient of determination (R2) 0.49. In contrast to controls (y=0.02+0.27x), for the 153 patients with AP (y=−0.16+0.58x) a higher R2 was determined (0.72 vs 0.29).

FIG. 3:

Correlation of glycoprotein 2 isoform a (GP2a) (A) and total GP2 (GP2t) (B) levels with disease duration. Serum GP2a and GP2t were detected in patients with acute pancreatitis (AP) with different disease severity by enzyme-linked immunosorbent assay.

I, mild AP; II, severe AP with local complications; Ill, severe AP with systemic complications; IV, severe AP with lethal outcome

FIG. 4:

Serum glycoprotein 2 isoform a (GP2a) (A) and total GP2 (GP2t) (B) levels in patients with acute pancreatitis (AP) and controls. GP2a and GP2t were analyzed in 153 patients with AP, 651 disease controls, 101 blood donors (BD) by enzyme-linked immunosorbent assay. Patients with AP were stratified into AP patients with up to three days of disease duration (n=12), between 4 and 10 days (n=47), and more than 10 days (n=94). As disease controls, 26 patients with chronic pancreatitis (CP), 125 with pancreatic cancer, 118 with liver cancer (LCa), 126 with gastrointestinal cancer (GICa), 40 with neuroendocrine tumor (NET), 40 with sarcoma (SA), 109 with benign liver and biliary diseases (bL/BD), 27 with peptic ulcer (PU), and 40 with peritonitis (PT) investigated. (Optimized cut-offs for GP2a and GP2t obtained by receiver-operating characteristic curve analysis were illustrated by dashed horizontal lines. Data are displayed in Box-and-Whisker plots with far out values, defined as values that are smaller than the lower quartile minus 3 times the interquartile range, or larger than the upper quartile plus 3 times the interquartile range, displayed as solid triangles.)

P, Kruskal Wallis test, post-hoc analysis

FIG. 5:

Comparison of assay accuracy of glycoprotein 2 isoform a (GP2a) and total GP2 (GP2t) detection by enzyme-linked immunosorbent assay. GP2a and GP2t were analyzed in 12 patients with acute pancreatitis as disease criterion and 752 controls as non-disease criterion and subjected to receiver-operating characteristic curve analysis. Optimal cut-off levels for GP2a and GP2t were determined at 0.7 and 2.3 ng/mL, respectively.

FIG. 6:

Correlation of glycoprotein 2 isoform a (GP2a) (A,C) and total GP2 (GP2t) (B,D) levels with procalcitonin (PCT) (A,B) and c-reactive protein (CRP) concentrations in 153 patients with acute pancreatitis. Optimized cut-offs for GP2a and GP2t obtained by receiver-operating characteristic curve analysis and generally accepted ones for CRP and PCT were illustrated by dashed horizontal and vertical lines, respectively. (Optimized cut-offs for GP2a and GP2t obtained by receiver-operating characteristic curve analysis as well as established cut-off of procalcitonin and C-reactive protein were illustrated by dashed lines.)

FIG. 7:

Serum glycoprotein 2 isoform a (GP2a), procalcitonin (PCT), and c-reactive protein (CRP) levels in follow-up samples of patients with acute pancreatitis (AP).

AP patients with available follow-up samples between the 2nd and 49th day of disease duration:

A, male, 47 years, alcohol abuse, severe AP with local complications

B, male, 31 years, alcohol abuse, severe AP with systemic complications

C, male, 48 years, alcohol abuse, severe AP with local complications

D, male, 31 years, alcohol abuse, severe AP with systemic complications

AP patients with late increase of GP2a (>10th day)

E, female, 65 years, biliary, severe AP with lethal outcome

F, female, 83 years, biliary, severe AP with lethal outcome

G, male, 59 years, alcohol abuse, severe AP with systemic complications

H, male, 26 years, alcohol abuse, severe AP with systemic complications

EXAMPLES

Without intending to be limiting, the invention will be explained in more detail with reference to an example.

Materials:

Subjects

Characteristics of the 153 patients with acute pancreatitis and 752 controls including 26 patients with CP, 125 with PCa, 118 with LCa, 126 with GICa, 40 with neuroendocrine tumors (NET), 40 with sarcoma (SA), 109 with benign liver or biliary disease (bL/BD), 27 with peptic ulcer (PU), 40 with peritonitis (PT), and 101 healthy blood donors (BD) are given in Table 4. According to disease severity, patients with acute pancreatitis were stratified retrospectively into mild and severe AP with local as well as systemic complications or lethal cases using clinical and imaging data.[10; 21] Furthermore, the etiology of AP (biliary, alcohol abuse, idiopathic, post-endoscopic retrograde cholangiopancreatography (ERCP), drug induced) was determined in accordance with international guidelines.[10] Sera of patients with AP and disease controls were collected at the department of surgery of the Otto-von-Guericke University Magdeburg. For 30 of the 152 patients with acute pancreatitis, 3 or more consecutive samples could be obtained. Thus, 128 additional samples were included into the study which covered a median observation period of 28 days (interquartile range [IQR] 28 days). Of note, disease duration from clinical onset of AP until first examination at the intensive care unit of the department of surgery was determined for all patients. For 152 and 146 AP patients, CRP and procalcitonin (PCT) levels could be obtained, respectively.

All clinical diagnoses were based upon standard clinical, imaging, endoscopic and histological criteria. The diagnosis of CP was established using a scoring system based on the presentation of calcifications or pancreatic duct abnormalities, evidence of pancreatic insufficiency, and abdominal pain, weight loss or glucose intolerance.[22]

The study was approved by the local ethics committee and complies with the World Medical Association Declaration of Helsinki regarding ethical conduct of research involving human subjects and/or animals. Aliquots of the sera stored at −80° C. were used to detect serum GP2 levels.

TABLE 4

Patients' and blood donors' (BD) characteristics

| disorder | Number (%) | Age (IQR) | Gender (f/m) |
| --- | --- | --- | --- |
| acute pancreatitis | 153 | 50.0 (28.0) | 58/95 |
| etiology | | | |
| alcohol abuse | 59 (38.6) | 40.0 (12.0) | 11/48 |
| biliary disease | 54 (35.3) | 65.0 (24.0) | 30/24 |
| drug induced | 1 (0.7) | 50.0 | 0/1 |
| idiopathic | 21 (13.7) | 61.0 (24.8) | 11/10 |
| post-trauma | 11 (7.2) | 57.0 (19.0) | 2/9 |
| post-ERCP | 7 (4.6) | 59.0 (39.5) | 4/3 |
| severity | | | |
| mild | 22 (14.4) | 57.5 (29.0) | 14/8 |
| local complications | 74 (48.4) | 45.5 (30.0) | 27/47 |
| systemic complications | 41 (26.8) | 54.0 (28.5) | 11/30 |
| lethal outcome | 16 (10.5) | 65.6 (29.0) | 6/10 |
| chronic pancreatitis | 26 | 48.0 (19.0)[§] | 13/13[&] |
| pancreatic cancer | 125 | 60.0 (16.0) | 68/57 |
| pancreatic carcinoma | 25 | 60.5 (15.2)[§] | 8/17[&] |
| papillary carcinoma | 36 | 63.0 (17.5) | 16/20[&] |
| pancreatic cystic neoplasm | 34 | 61.0 (16.0) | 27/7 |
| IPMN | 18 | 64.0 (12.0) | 10/8[&] |
| islet cell tumor | 12 | 49.0 (14.5)[§] | 7/5[&] |
| liver cancer | 118 | 64.0 (11.0) | 59/59 |
| hepatocellular cancer | 40 | 64.0 (12.2) | 20/20[&] |
| cholangiocelluar cancer | 38 | 63.0 (8.2) | 19/19[&] |
| cholangiocelluar cystadenocarcinoma | 40 | 66.0 (9.0) | 20/20[&] |
| gastrointestinal cancer | 126 | 63.3 (16.8) | 54/72[&] |
| Barrett's esophagus | 26 | 63.5 (9.5) | 6/20[&] |
| gastric cancer | 40 | 69.0 (14.2) | 20/20[&] |
| GIST | 26 | 62.5 (16.5) | 11/15[&] |
| colon carcinoma | 34 | 58.0 (24.2)[§] | 17/17[&] |
| neuroendocrine tumors | 40 | 62.5 (19.5) | 20/20[&] |
| sarcoma | 40 | 61.0 (16.2) | 20/20[&] |
| benign liver/biliary disease | 109 | 56.0 (24.0) | 78/31 |
| benign liver disease | 46 | 43.5 (23.8) | 38/8 |
| hepatic cyst | 23 | 59.0 (9.0)[§] | 20/3 |
| benign biliary disease | 40 | 61.0 (19.8) | 20/20[&] |
| peptic ulcer | 27 | 63.0 (12.0) | 7/20[&] |
| peritonitis | 40 | 66.0 (24.8) | 20/20[&] |
| blood donors | 101 | 27.5 (15.0) | 39/62[&] |

ERCP, endoscopic retrograde cholangiopancreatography;
f, female;
GIST, gastrointestinal stromal tumor;
IPMN, intraductal papillary mucinous neoplasm;
IQR, interquartile range;
m, male
[§]age not significantly different to the age of patients with acute pancreatitis ($p > 0.05$)
[&]gender distribution not significantly different to the one of patients with acute pancreatitis ($p > 0.05$)

Anti-GP2 Antibody Production

Human GP2a and GP2b were expressed in the baculovirus system as described elsewhere. Briefly, the plasmids pcDNA3.1+GP2-trunc-Thrombin-His (GP2a, CCS GmbH, Hamburg, Germany) and pBluescript-GP2 (GP2b, Thermo-Scientific, Braunschweig, Germany) were used which code the respective isoform amino-acid sequences. At the C-terminal end, the GPI anchor was replaced by a His6-Tag. The two isoforms were cloned into pVL1392, respectively and resulting constructs were verified by sequencing. Transfection into and culture of insect *Spodoptera frugiperda* (Sf) 9 cells was performed as described elsewhere.[23] GP2 isoforms were purified from harvested supernatants by Ni-chelate chromatography.

Polyclonal antibodies to GP2 were produced immunising rabbits with recombinant human GP2 isoforms according to a standard immunisation protocol (three cycles of injection of 100 µg protein). They were purified by affinity chromatography employing recombinant GP2a immobilized to sephadex.

Monoclonal antibodies recognizing GP2a and GP2b isoforms were developed by immunizing Balb/c mice with modified immunoconjugates. GP2 isoforms were coupled to the major capsid protein VP1 of hamster polyomavirus (HaPyV) via glutaraldehyde linking according to standard procedures. The expression of recombinant HaPyV-VP1 and the immunization procedure were performed as previously reported.[24] The selection of GP2-specific monoclonal antibodies was performed by ELISA as described elsewhere. [25]

ELISA for the Detection of GP2a and GP2t

GP2a and GP2t were assessed in serum samples of patients and controls by ELISAs. The monoclonal anti-GP2a antibody K9 or polyclonal rabbit anti-GP2 antibodies at a concentration of 1 μg/mL were coated onto Maxisorb microtiter plates (Nunc, Roskilde, Denmark) in coating buffer (pH=9.5) at 4° C. over night. After blocking with 1% (w/v) bovine serum albumin in 50 mM Tris-buffered saline (pH=7.4) (Sigma Co, Taufkirchen, Germany) at room temperature for one hour, plates were sealed for further use. For the detection of GPa and GPt, serum samples diluted 1 in 100 in 50 mM Tris-buffered saline (pH=7.4) with 0.2% BSA (w/v) were incubated at room temperature for 1 hour and washed with Tris-buffered saline containing 0.1% (v/v) Tween 20 (Sigma). Horseradish peroxidase (HRP)-labeled anti-human polyclonal GP2 antibodies were added and developed with ready-to-use hydrogen peroxide/tetramethylbenzidine substrate (Seramun, Heidesee, Germany). Conjugation of affinity purified polyclonal anti-GP2 antibodies to HRP was done by the sodium periodate technique as described elsewhere.[26]

The reaction was stopped with 0.25 mol/l sulphuric acid after 15 min. The optical density of the samples was read using a microplate reader (SLT, Crailsheim, Germany) at a wavelength of 450 nm/620 nm. Purified recombinant GP2a was used as standard material and GP2 levels were expressed in ng/mL.

For interference experiments, GP2 containing sera were spiked with hemoglobulin, triglycerides, bilirubin, and GP2's urinary homolog Tamm-Horsfall protein (uromodulin) (Sigma Co). Final concentrations were 0.0-2.5 g/L for hemoglobin, 30.0-100.0 mg/L for bilirubin, 5.7-25.0 g/L for triglycerides and 0.0-10.0 g/L for uromodulin.

Statistical Analysis

A Kolmogorov-Smirnov test was used to reject the normal distribution of data. Thus, measured values were expressed as medians with IQR. The two-tailed, non-parametric Kruskal-Wallis test was used to test for statistically significant differences of independent samples in 2 or more groups. Comparison of independent samples between two groups was performed by two-tailed Mann-Whitney test.

Spearman's rank correlation test was applied for within group comparison. Comparison of prevalence rates between groups was performed by two-tailed Fisher's exact test. P values of less than 0.05 were considered significant. Assay performance and the comparison thereof were analyzed by receiver-operating characteristics (ROC) curve analysis. All calculations were performed using Medcalc statistical software (Medcalc, Mariakerke, Belgium).

Example 1: Development of Anti-GP2 ELISA

For the development of anti-GP2 ELISA, one monoclonal antibody to GP2a, coded K9, could be generated with a special immunization protocol which was needed due to several unsuccessful attempts to immunize mice with human recombinant GP2a. K9 recognized soluble recombinant GP2a readily in its native and denaturated state, but not GP2b when used as solid-phase immobilized antibody in ELISA (FIG. 1). In contrast, the sole monoclonal antibody P102 generated successfully to the shorter isoform GP2b interacted with both immobilized isoforms in ELISA but with soluble GP2 at a low binding strength only which did not allow to develop a sensitive ELISA for GP2b (FIG. 1). Thus, K9 was employed as a solid-phase antibody for the development of an ELISA for the analysis of GP2a and affinity-purified rabbit polyclonal anti-GP2 antibodies for the assessment of GP2t, respectively. Subsequently, bound GP2a and GP2t were detected by HRP-labelled polyclonal affinity purified anti-GP2 antibodies.

Example 2: Regression of GP2a and GP2t Levels

Figure 2:
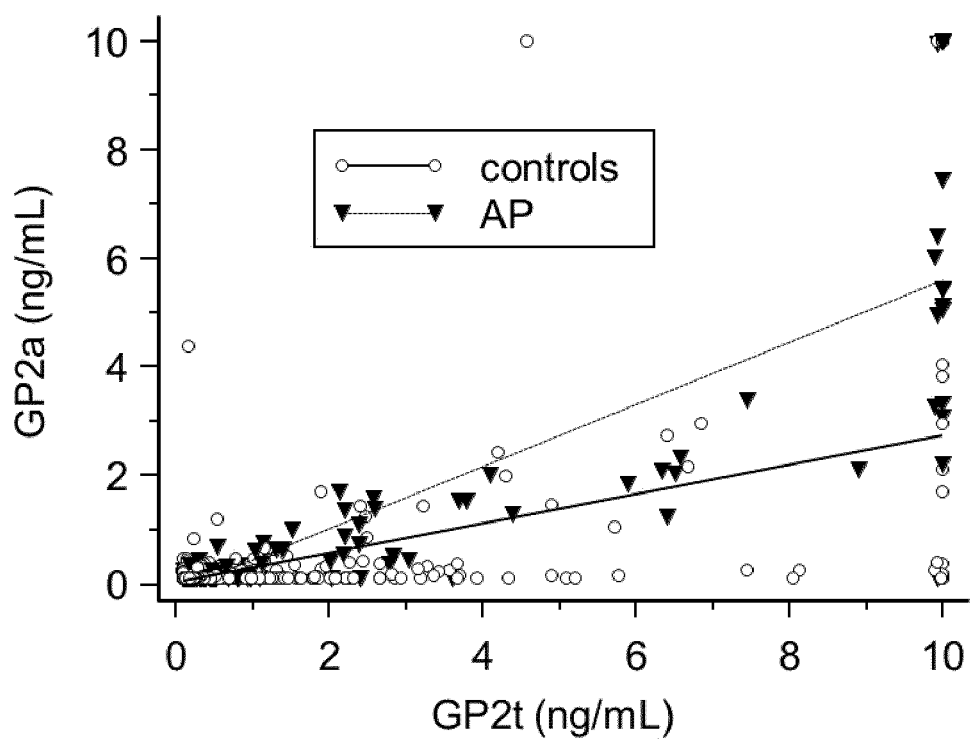

As expected, GP2a and GP2t levels were linearly related to each other (y=−0.05+0.41x, coefficient of determination $[R^2]$=0.49) when samples of all AP patients and controls are analyzed (FIG. 2). However, regression analysis in AP patients alone revealed a higher $R^2$ of 0.72 compared to controls ($R^2$=0.29) and a significantly different slope and intercept (p<0.0001, =0.0001, respectively). This indicates a poorer association of GP2a and GP2t levels in controls compared to AP patients.

Example 3: Correlation GP2a and GP2t Levels with Disease Duration

Figure 3:
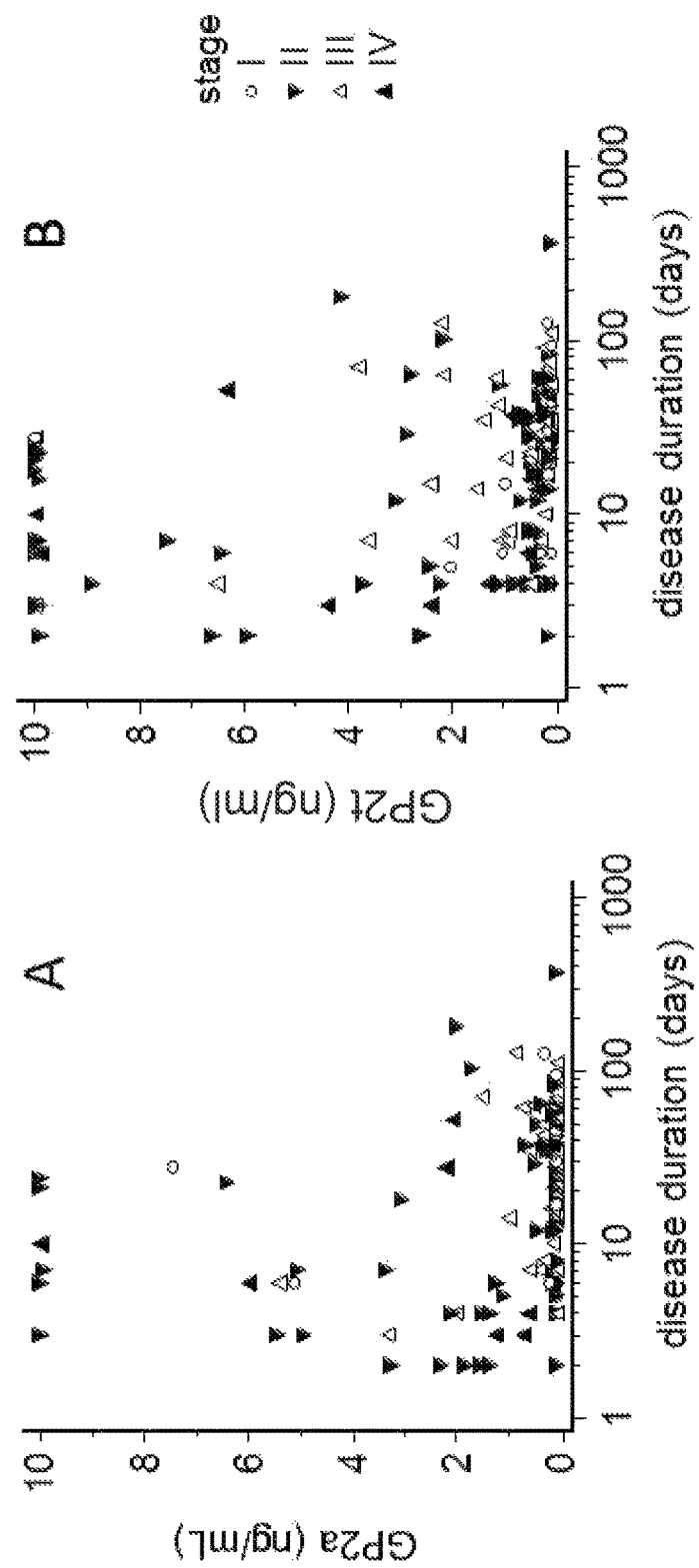

Interestingly, both GP2a and GP2t demonstrated a significantly negative correlation with disease duration in AP (FIG. 3) (Spearmen's coefficient of rank correlation [rho]=−0.22, 95% confidence interval [CI]−0.37-−0.07, p=0.0053; rho=−0.41, 95% CI −0.54-−0.27, p<0.0001; respectively). For further evaluation, patients with AP were stratified into 3 groups covering samples of AP patients with disease duration of <=3 days (n=12), with disease duration from 4 to 10 days (n=47) and greater than 10 days (n=94) (Table 5).

TABLE 5

Prevalences of total GP2 (GP2t) and isoform alpha (GP2a) positives detected by enzyme-linked immunosorbent assay (ELISA) in 153 patients with acute pancreatitis and 752 controls employing 2.3 and 0.7 ng/mL as optimized cut-offs, respectively.

| disorder | n | GP2a (%) | GP2t (%) |
|---|---|---|---|
| acute pancreatitis | 153 | 40 (26.1) | 39 (25.5) |
| disease duration | | | |
| <=third disease day | 12 | 11 (91.7)[§§§] | 11 (91.7)[§§§] |
| <=fourth disease day | 30 | 16 (53.3)[§§,&] | 14 (46.7)[§,&] |
| <=tenth disease day | 59 | 26 (44.1)[§,&&] | 25 (42.4)[§,&&] |
| etiology | | | |
| alcohol abuse | 59 | 19 (32.2) | 17 (28.8) |
| biliary disease | 54 | 9 (16.7) | 8 (14.8) |
| drug induced | 1 | 1 (100.0) | 1 (100.0) |
| idiopathic | 21 | 8 (38.1) | 9 (42.9) |
| post-trauma | 11 | 3 (27.3) | 4 (36.4) |
| post-ERCP | 7 | 0 (0.0) | 0 (0.0) |
| severity | | | |
| mild | 22 | 2 (9.1) | 2 (9.1) |
| local complications | 74 | 24 (32.4) | 25 (33.8) |
| systemic complications | 41 | 7 (17.1) | 6 (14.6) |
| lethal outcome | 16 | 7 (43.8) | 6 (37.5) |
| disease controls and blood donors | 752 | 28 (3.7)[§§§, &&&] | 56 (7.4)[§§§, &&&] |
| chronic pancreatitis | 24 | 3 (12.5)[&&&] | 3 (12.5)[&&&] |
| pancreatic cancer | 125 | 11 (8.8)[§§§, &&&] | 14 (11.2)[§§, &&&] |

TABLE 5-continued

Prevalences of total GP2 (GP2t) and isoform alpha (GP2a) positives
detected by enzyme-linked immunosorbent assay (ELISA) in 153
patients with acute pancreatitis and 752 controls employing
2.3 and 0.7 ng/mL as optimized cut-offs, respectively.

| disorder | n | GP2a (%) | GP2t (%) |
|---|---|---|---|
| pancreatic carcinoma | 25 | 2 (8.0)$^{\S, \&\&\&}$ | 4 (16.0)$^{\&\&\&}$ |
| papillary carcinoma | 36 | 4 (11.1)$^{\&\&\&}$ | 5 (13.9)$^{\&\&\&}$ |
| pancreatic cystic neoplasm | 34 | 1 (2.9)$^{\S\S, \&\&\&}$ | 3 (8.8)$^{\S, \&\&\&}$ |
| IPMN | 18 | 3 (16.7)$^{\&\&\&}$ | 2 (11.1)$^{\&\&\&}$ |
| islet cell tumor | 12 | 1 (8.3)$^{\&\&}$ | 0 (0.0)$^{\&\&\&}$ |
| liver cancer | 118 | 5 (4.2)$^{\S\S\S, \&\&\&}$ | 18 (15.2)$^{\&\&\&}$ |
| hepatocellular cancer | 40 | 1 (2.5)$^{\S\S\S, \&\&\&}$ | 9 (22.5)$^{\&\&}$ |
| cholangiocelluar cancer | 38 | 2 (5.3)$^{\S\S, \&\&\&}$ | 5 (13.2)$^{\&\&\&}$ |
| cholangiocelluar cystadenocarcinoma | 40 | 2 (5.0)$^{\S\S, \&\&\&}$ | 4 (10.0)$^{\&\&\&}$ |
| gastrointestinal cancer | 126 | 2 (1.6)$^{\S\S\S, \&\&\&}$ | 6 (4.8)$^{\S\S\S, \&\&\&}$ |
| Barrett's esophagus | 26 | 0 (0.0)$^{\S\S, \&\&\&}$ | 0 (0.0)$^{\S, \&\&\&}$ |
| gastric cancer | 40 | 1 (2.5)$^{\S\S, \&\&\&}$ | 3 (7.5)$^{\S, \&\&\&}$ |
| GIST | 26 | 0 (0.0)$^{\S\S, \&\&\&}$ | 1 (3.8)$^{\S, \&\&\&}$ |
| colon carcinoma | 34 | 1 (2.9)$^{\S\S, \&\&\&}$ | 2 (5.9)$^{\S, \&\&\&}$ |
| neuroendocrine tumors | 40 | 1 (2.5)$^{\S\S, \&\&\&}$ | 3 (7.5)$^{\S, \&\&\&}$ |
| Sarcoma | 40 | 1 (2.5)$^{\S\S, \&\&\&}$ | 1 (2.5)$^{\S\S, \&\&\&}$ |
| benign liver/bilebladder disease | 109 | 2 (1.8)$^{\S\S\S, \&\&\&}$ | 2 (1.8)$^{\S\S\S, \&\&\&}$ |
| benign liver disease | 46 | 0 (0.0)$^{\S\S\S, \&\&\&}$ | 0 (0.0)$^{\S\S\S, \&\&\&}$ |
| hepatic cyst | 23 | 1 (4.3)$^{\S, \&\&\&}$ | 1 (4.3)$^{\S, \&\&\&}$ |
| benign bilebladder disease | 40 | 1 (2.5)$^{\S\S, \&\&\&}$ | 1 (2.5)$^{\S\S\S, \&\&\&}$ |
| peptic ulcer | 27 | 1 (3.7)$^{\S\S, \&\&\&}$ | 2 (7.4)$^{\S, \&\&\&}$ |
| peritonitis | 40 | 2 (5.0)$^{\S\S, \&\&\&}$ | 5 (12.5)$^{\&\&\&}$ |
| blood donors | 101 | 0 (0.0)$^{\S\S\S, \&\&\&}$ | 2 (2.0)$^{\S\S\S, \&\&\&}$ |

GIST, gastrointestinal stromal tumor;
IPMN, intraductal papillary mucinous neoplasm;
$^{\S}$ p < 0.05;
$^{\S\S}$ p < 0.01;
$^{\S\S\S}$ p < 0.0001; comparison of GP2 prevalence with the one in all acute pancreatitis cases by Fisher's test;
$^{\&}$ p < 0.05;
$^{\&\&}$ p < 0.01;
$^{\&\&\&}$ p < 0.0001; comparison of GP2 prevalence with the one in acute pancreatitis <= third disease day by Fisher's test;

Example 4: Comparison of GP2a and GP2t Levels in AP and Control Groups

Patients with AP were age and gender matched with patients suffering from CP, PCa, islet cellular tumor, and colon carcinoma (p>0.05, Kruskal Wallis test and Post hoc analysis, Fisher's test, respectively).

Figure 4:
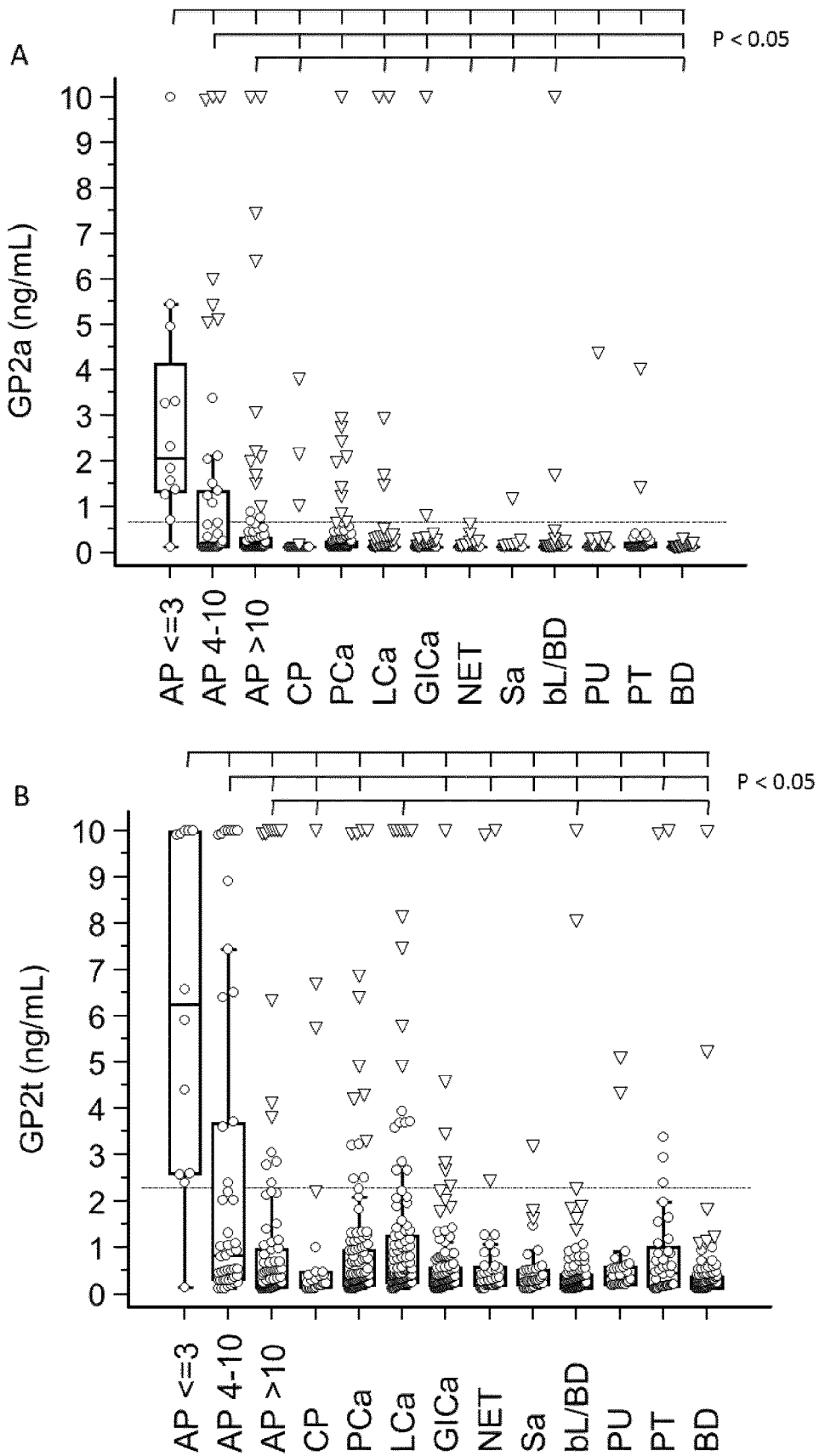

Serum GP2a and GP2t determined by ELISAs demonstrated significantly different levels in 153 patients with AP and 752 controls (p<0.0001, Kruskal Wallis test) (FIG. 4A,B). Thus, median levels of GP2a and GP2t in AP patients with disease duration <=3 days, with disease duration from 4 to 10 days, and with disease duration >10 days from the first day of occurrence of clinical symptoms demonstrated a significant decline from time period to time period (Post hoc analysis, p>0.05, respectively). The median GP2a and GP2t levels in AP patients until the 3rd day of disease duration were significantly elevated in comparison with all control groups including patients with chronic pancreatitis (Post hoc analysis, p<0.05, respectively). The median GP2t level of AP patients with >10 days disease duration was additionally not different in patients with GICa, NET, SA and even CP (Post hoc analysis, p<0.05, respectively).

Example 5: Comparison of GP2a and GP2t Assay Performance

Figure 5:
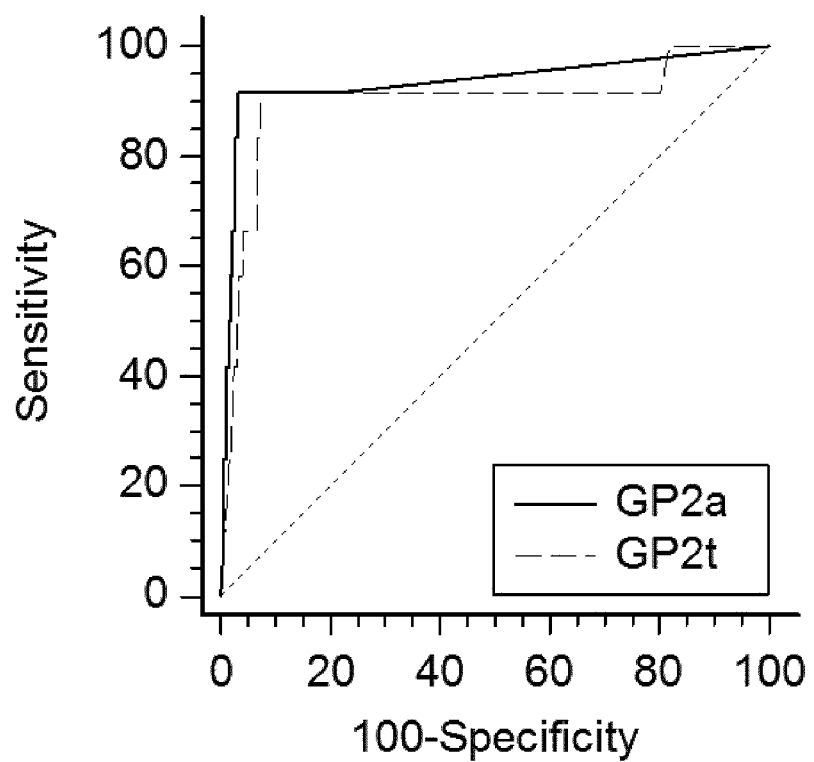

To take into consideration the declining GP2 levels over time, respective optimized GP2 cut-offs for the discrimination of AP patients from controls were obtained by ROC curve analysis employing AP patients till the 3rd disease day as positive criterion and all 752 disease controls and BD as negative criterion (FIG. 5). The comparison of ROC curves revealed a significantly higher area under the curve (AUC) for GP2a in the first 3 disease days in contrast to GP2t (FIG. 5) (0.93, 95% CI: 0.91-0.95 vs 0.90, 95% CI: 0.88-0.92, p=0.0427). Thus, the GP2a ELISA possessed a significantly better assay accuracy with a sensitivity of 91.7% (95% CI: 61.5%-99.8%) and a specificity of 96.7% (95% CI: 95.1%-97.8%). The GP2t ELISA did demonstrate the same sensitivity but a poorer specificity of 92.6% (95% CI: 90.4%-94.3%). Altogether, these data resulted in a positive likelihood ratio (LR) of 24.6 (95% CI: 16.5-36.8) and a -LR of 0.09 (95% CI: 0.01-0.57) for GP2a whereas the +LR of GP2t reached 12.3 (95% CI: 9.1-16.7) at the same -LR like GP2a only.

Example 6: Comparison of GP2a and GP2t Positivity in AP Patients and Controls The cut-offs obtained by ROC curve analysis of 0.7 ng/mL for GP2a and 2.3 ng/mL for GP2t were used to define the prevalence of positives in AP patients and controls (Table 5). There was a remarkable decrease in the prevalence of GP2a and GP2t positives after the 3rd disease day (53.3% and 46.7%, respectively). Within the first 10 days of disease duration the prevalence dropped to 44.1% and 42.4%, respectively.

The GP2a ELISA revealed significantly less false positives compared with the GP2t assay (28/752 vs 56/752, p=0.0022). This was basically due to the significantly higher prevalence of false positive GP2t findings in contrast to GP2a ones in patients with liver cancer (18/118 vs 5/118, p=0.0073) and here in particular in patients with hepatocellular cancer (9/40 vs 1/40, p=0.0143).

Example 7: GP2a and GP2t Levels and Positivity in Etiological AP Variants

GP2a and GP2t levels were significantly different in the 153 AP patients with varying etiology (Kruskal-Wallis test, p=0.0144 and 0.0199, respectively). In accordance with Post-hoc analysis, patients with idiopathic and alcoholic AP demonstrated significantly elevated GP2a and GP2t levels in contrast to AP patients with biliary disease and post-trauma AP (p<0.05, respectively). The respective differences in the prevalence of GP2a positivity, however, did not reach significance (p=0.0803, 0.0657). In contrast, there was a significantly higher prevalence of GP2t in AP patients with idiopathic disease compared with biliary AP patients (9/21 vs 8/54, p=0.0143). Of note, disease duration was not significantly different in the AP patient groups with various etiology (Kuskal-Wallis test, p=0.0997).

Example 8: Correlation of GP2a and GP2t with CRP and PCT

Figure 6:
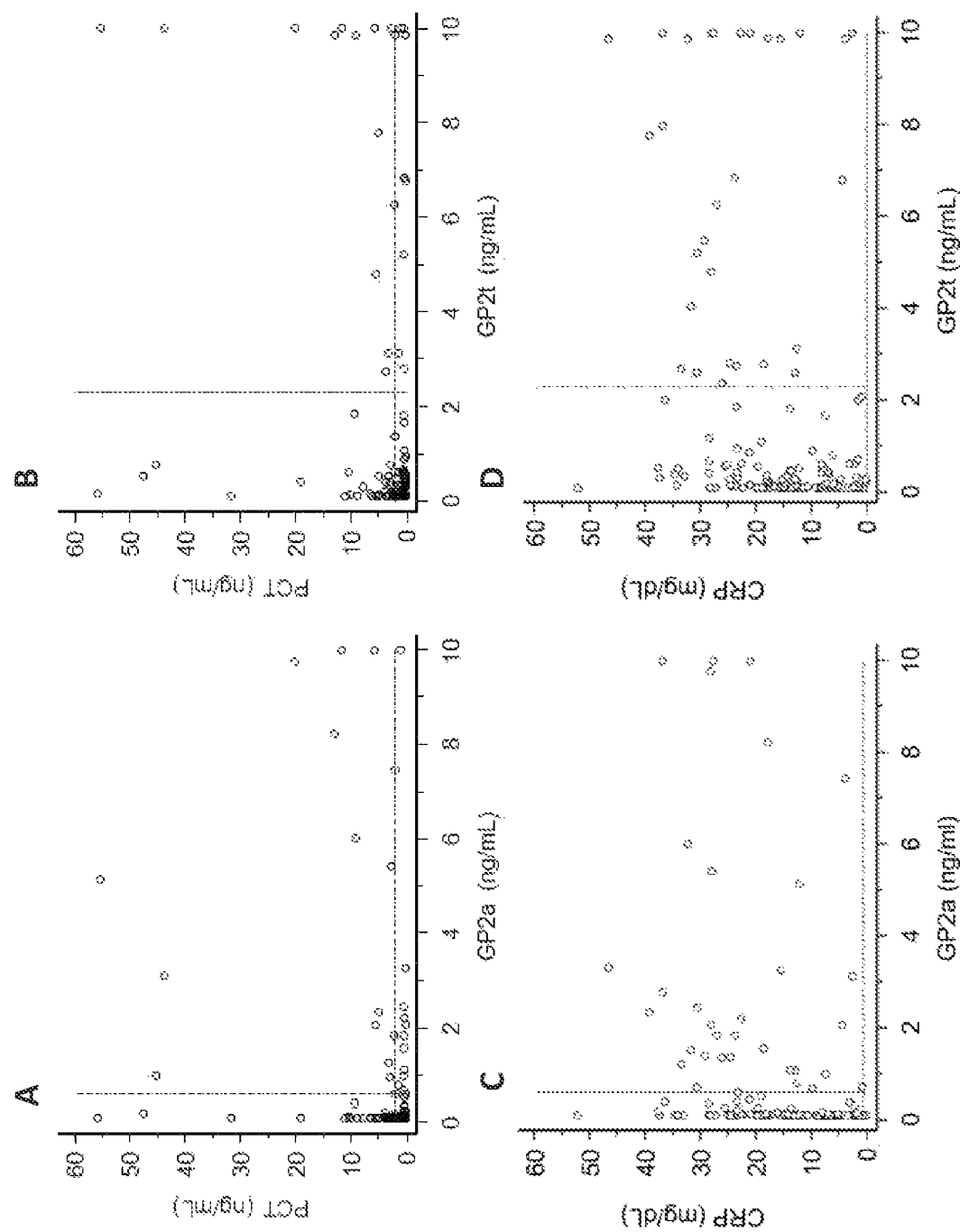

GP2a and GP2t levels were significantly correlated with PCT (rho=0.21, 95% CI: 0.05-0.36 and 0.26, 95% CI: 0.11-0.41; p=0.0110 and 0.0012; respectively) as well as CRP values (rho=0.37, 95% CI: 0.22-0.50 and 0.40, 95% CI: 0.26-0.53; p<0.0001; respectively) in 152 and 146 follow-up samples of AP patients, respectively (FIG. 6).

In general, GP2a and GP2t levels declined rapidly after the 3rd disease day. However, patients with severe AP demonstrated elevated GP2a levels until the 21st day of disease duration with a steady decline over time (FIG. 7A). In particular CRP levels demonstrated a similar modulation which corresponded with the therapy success (FIGs. 7A,B,C,D). In severe cases with lethal outcome, there was a strikingly similar behavior of GP2a and PCT levels at time points beyond the 10th disease duration day (FIG. 7E,F). In these two cases, a combined elevation of GP2a and PCT shortly before death of the patients could be observed. Furthermore, the AP patient illustrated in FIG. 7E showed an interestingly simultaneous increase and subsequent decrease of GP2a and PCT levels in response to major intestinal surgery on disease day 34. Of note, increases in GP2a levels could be determined even later than the 50th disease duration day (FIG. 7G,H). GP2t levels showed similar alterations like GP2a (data not shown).

Example 9: Prediction of AP Severity by GP2a and GP2t Levels

Given the established association of GP2a and GP2t levels with the disease severity markers PCT and CRP in follow-up samples, AP patients were stratified in 4 groups according to disease severity: I mild AP, II severe disease with local complications, III severe disease with systemic complications, and IV severe disease with lethal outcome, retrospectively. There was a tendency for a higher prevalence of GP2a and GP2t positivity in the 131 patients with severe AP (11, III, IV) compared to the 22 patients with mild AP (p=0.0650 and 0.0660, respectively). Of note, there was a significant difference of GP2a positivity with a lower cut-off of 0.4 ng/mL obtained by ROC curve analysis with all 153 AP patients included (45/131 vs 2/22, p=0.0226). Similar lowering of the cut-off for GP2t did not result in a significant differentiation of mild and severe AP.

Remarkably, AP patients with lethal outcome during the observation period did demonstrate a significantly higher prevalence of GP2a and GP2t compared with mild cases on the day of admission to the intensive care surgery unit (7/16 vs 2/22, 6/16 vs 2/22, p=0.0211, 0.0497; respectively). This resulted in an odds ratio of 7.8 (95% CI: 1.3-45.1, p=0.0222) for GP2a and 6.0 (95% CI: 1.0-35.3, p=0.0474) for GP2t positivity regarding the prognosis for a lethal outcome in AP on the day of admission. When AP patients admitted until the 10th disease day were considered only, there was also a significantly higher GP2a positivity in AP patients with lethal outcome compared to patients with mild disease (5/6 vs 1/7, p=0.0291).

Example 10: Assay Performance of the GP2a ELISA

Since GP2a testing proofed to be superior in terms of diagnostic accuracy, assay performance of this ELISA was analyzed for routine use. The limit of detection of GP2a was determined at 0.2 ng/mL by using recombinant GP2a.

Linearity was evaluated by diluting a sample with a high GP2a concentration with increasing amounts (from 0% to 100% in increments of 20%) of a sample that did not contain GP2a from 0.5 ng/mL to 6 ng/mL. There was good linearity with a $R^2$ values of 0.99 for GP2a.

The intra-assay and inter-assay coefficients of variation (CV) were analyzed using sera with varying concentrations of GP2a in accordance with the CLSI protocol EP15-A2. The intra-assay CVs ranged from 6.4% to 15.0% and inter-assay CV from 7.7% to 30.0% for GP2a levels from 3.9-0.2 ng/mL, respectively (Table 6).

Recovery experiments for the assessment of GP2a were conducted by spiking human serum devoid of GP2a with recombinant GP2a. Recovery of GP2a and GP2t ranged from 92.3%-113.6% for spiked GP2a and GP2t levels of 0.25-1.25 ng/mL.

For interference experiments, GP2 containing sera were spiked with hemoglobulin, triglycerides, bilirubin and GP2's urinary homolog Tamm-Horsfall protein (uromodulin) which is synthesized in the tubular cells of the thick ascending limb and the early distal tubule in the kidneys. Final concentrations of 1.0 g/L hemoglobin, 30.0 mg/L bilirubin, 25.0 g/L triglycerides, and 10.0 g/L uromodulin did not interfere with the measurement of GP2a levels.

TABLE 6

Intra and inter-assay variation of the enzyme-linked immunosorbent assay for the detection of the alpha isoform of glycoprotein 2 (GP2a). The intra-assay and inter-assay coefficients of variation (CV) were analyzed using sera with varying concentrations of GP2a. Intra-assay CV was determined by eight measurements for each serum while inter-assay CV was assessed by analyzing eight determinations for each serum on five different days in accordance with the CLSI protocol EP15-A2.

| Intra-assay variance | | | |
|---|---|---|---|
| GP2a (ng/mL) n = 8 | 3.9 | 0.8 | 0.2 |
| SD | 0.25 | 0.08 | 0.03 |
| CV % | 6.4 | 10.0 | 15.0 |
| Inter-assay variance | | | |
| GP2a (ng/mL) 5 days | 3.9 | 0.8 | 0.2 |
| SD | 0.30 | 0.08 | 0.06 |
| CV % | 7.7 | 10.0 | 30.0 |

SD, standard deviation

Abbreviations

AP, acute pancreatitis; AUC, area under the curve; BMI; body mass index; CP, chronic pancreatitis, BD, blood donor; CI, confidence interval; CV, coefficient of variation; ERCP, endoscopic retrograde cholangiopancreatography; ELISA, enzyme-linked immunosorbent assay; GICa, gastrointestinal cancer; GIST, gastrointestinal stromal tumor; GP2, zymogen granule membrane glycoprotein 2; GPI, glycosyl phosphatidylinositol; IPMN, intraductal papillary mucinous neoplasm; IQR, interquartile range; LCa, liver cancer; LR, likelihood ratio; NET, neuroendocrine tumor; PCa, pancreatic cancer; PT, peritonitis; PU, peptic ulcer; rho, Spearman's rank coefficient of correlation; ROC, receiver-operating characteristics; SA, sarcoma; SD, standard deviation; ZG, zymogen granules.

LITERATURE

1 Peery A F, Dellon E S, Lund J et al. Burden of gastrointestinal disease in the United States: 2012 update. Gastroenterology. 2012; 143:1179-1187.
2 Lippi G, Valentino M, Cervellin G. Laboratory diagnosis of acute pancreatitis: in search of the Holy Grail. Crit Rev Clin Lab Sci. 2012; 49:18-31.
3 Muller C A, Appelros S, Uhl W et al. Serum levels of procarboxypeptidase B and its activation peptide in patients with acute pancreatitis and non-pancreatic diseases. Gut. 2002; 51:229-235.
4 Lankisch P G, Apte M, Banks P A. Acute pancreatitis. Lancet. 2015; 386:85-96. Afghani E, Pandol S J, Shimosegawa T et al. Acute Pancreatitis-Progress and Challenges: A Report on an International Symposium. Pancreas. 2015; 44:1195-1210.
6 Lerch M M, Halangk W. Human pancreatitis and the role of cathepsin B. Gut. 2006; 55:1228-1230.
7 Sendler M, Maertin S, John D et al. Cathepsin-B activity initiates apoptosis via digestive protease activation in pancreatic acinar cells and experimental pancreatitis. J Biol Chem. 2016.
8 Leppkes M, Maueroder C, Hirth S et al. Externalized decondensed neutrophil chromatin occludes pancreatic ducts and drives pancreatitis. Nat Commun. 2016; 7:10973.
9 Meher S, Mishra T S, Sasmal P K et al. Role of Biomarkers in Diagnosis and Prognostic Evaluation of Acute Pancreatitis. J Biomark. 2015; 2015:519534.
10 Banks P A, Bollen T L, Dervenis C et al. Classification of acute pancreatitis—2012: revision of the Atlanta classification and definitions by international consensus. Gut. 2013; 62:102-111.
11 Keim V, Teich N, Fiedler F et al. A comparison of lipase and amylase in the diagnosis of acute pancreatitis in patients with abdominal pain. Pancreas. 1998; 16:45-49.
12 Da B L, Shulman I A, Joy L C et al. Origin, Presentation, and Clinical Course of Nonpancreatic Hyperlipasemia. Pancreas. 2016; 45:846-849.
13 Mantke R, Pross M, Kunz D et al. Soluble thrombomodulin plasma levels are an early indication of a lethal course in human acute pancreatitis. Surgery. 2002; 131:424-432.
14 Mofidi R, Suttie S A, Patil P V et al. The value of procalcitonin at predicting the severity of acute pancreatitis and development of infected pancreatic necrosis: systematic review. Surgery. 2009; 146:72-81.
15 Lowe A W, Luthen R E, Wong S et al. The Level of the Zymogen Granule Protein GP2 Is Elevated in a Rat Model for Acute Pancreatitis. Gastroenterology 1994, 107. 1994; 107:1819-1827.
16 Rindler M J, Hoops T C. The pancreatic membrane protein GP-2 localizes specifically to secretory granules and is shed into the pancreatic juice as a protein aggregate. Eur J Cell Biol. 1990; 53:154-163.
17 Havinga J R, Slot J W, Strous G J. Membrane detachment and release of the major membrane glycoprotein of secretory granules in rat pancreatic exocrine cells. Eur J Cell Biol 1985 November; 39(1):70-6. 1985; 39:70-76.
18 LeBel D, Beattie M. The major protein of pancreatic zymogen granule membranes (GP-2) is anchored via covalent bonds to phosphatidylinositol. Biochem Biophys Res Commun. 1988; 154:818-823.
19 Fukuoka S. Molecular cloning and sequences of cDNAs encoding alpha (large) and beta (small) isoforms of human pancreatic zymogen granule membrane-associated protein GP2. Biochim Biophys Acta. 2000; 1491:376-380.
20 Hao Y, Wang J, Feng N et al. Determination of plasma glycoprotein 2 levels in patients with pancreatic disease. Arch Pathol Lab Med. 2004; 128:668-674.
21 Lerch M M. Classifying an unpredictable disease: the revised Atlanta classification of acute pancreatitis. Gut. 2013; 62:2-3.
22 Hoffmeister A, Mayerle J, Beglinger C et al. English language version of the S3-consensus guidelines on chronic pancreatitis: Definition, aetiology, diagnostic examinations, medical, endoscopic and surgical management of chronic pancreatitis. Z Gastroenterol. 2015; 53:1447-1495.
23 Roggenbuck D, Reinhold D, Wex T et al. Autoantibodies to GP2, the major zymogen granule membrane glycoprotein, are new markers in Crohn's disease. Clin Chim Acta. 2011; 412:718-724.
24 Messerschmidt K, Hempel S, Holzlohner P et al. IgA antibody production by intrarectal immunization of mice using recombinant major capsid protein of hamster polyomavirus. Eur J Microbiol Immunol (Bp). 2012; 2:231-238. Roggenbuck D, Rober N, Bogdanos D P et al. Autoreactivity to isoforms of glycoprotein 2 in inflammatory bowel disease. Clin Chim Acta. 2015; 442:82-83.
26 Wilson M B, Nakane P K. The covalent coupling of proteins to periodate-oxidized sephadex: a new approach to immunoadsorbent preparation. J Immunol Methods. 1976; 12:171-181.
27 Wong S M, Lowe A W. Sequence of the cDNA encoding human GP-2, the major membrane protein in the secretory granule of the exocrine pancreas. Gene. Vol. 171, no. 2, 1 Jun. 1996 (1996-06-01), pages 311-312.

The invention claimed is:

1. An in vitro method for diagnosis and treatment of acute pancreatitis (AP) in a human subject exhibiting symptoms of pancreatic disease by detection of Glycoprotein 2 isoform alpha (GP2a) protein, comprising:
   providing a sample of the human subject exhibiting symptoms of pancreatic disease, wherein said sample is obtained from the subject within 72 hours of the appearance of said symptoms,
   providing an affinity reagent directed against GP2a,
   contacting said sample with said affinity reagent thereby capturing GP2a from said sample, and
   determining a concentration of GP2a greater than 0.7 ng/ml in said sample diagnosing, based on the concentration of GP2a, a presence of AP and an absence of chronic pancreatitis and pancreatic cancer, and
   administering an AP specific treatment of the patient.

2. The method according to claim 1, wherein the GP2a comprises or consists of a protein with an amino acid sequence according to SEQ ID NO: 1 or 2.

3. The method according to claim 1, wherein the affinity reagent specifically binds the GP2a with no binding or negligible binding to Glycoprotein 2 isoform beta (GP2b).

4. The method according to claim 3, wherein said affinity reagent is a monoclonal antibody.

5. The method according to claim 4, wherein said monoclonal antibody binds specifically the GP2a, with no binding or negligible binding to the GP2b in both native and denaturated sample conditions.

6. The method according to claim 1, wherein the method is conducted as an Enzyme Linked Immunosorbent Assay (ELISA), wherein said affinity reagent is immobilized on a solid surface before contacting said sample.

7. The method according to claim 6, wherein the determination of the GP2a concentration comprises:
   a) capturing the GP2a from the sample via the affinity reagent that is immobilized to the solid surface to create a captured GP2a,
   b) treating said captured GP2a with a labelled secondary affinity reagent directed to GP2,
   c) detecting a signal emitted from said labelled secondary affinity reagent directed to GP2, and
   d) comparing the signal obtained from said labelled secondary affinity reagent with the signal from one or more control samples of pre-determined GP2a concentration.

8. The method according to claim 7, wherein the signal is obtained from horseradish peroxidase conjugated to the secondary affinity reagent.

9. The method according to claim 1, wherein the sample is a blood sample, a plasma sample or a serum sample.

10. The method according to claim 3, wherein the affinity reagent specifically binds GP2a comprising or consisting of a protein with an amino acid sequence according to SEQ ID NO 1 or 2, with no binding or negligible binding to GP2b comprising or consisting of a protein with an amino acid sequence according to SEQ ID NO 3 or 4.

11. The method according to claim 5, wherein said antibody binds specifically GP2a comprising or consisting of a protein with an amino acid sequence according to SEQ ID NO 1 or 2, with no binding or negligible binding to GP2b comprising or consisting of a protein with an amino acid sequence according to SEQ ID NO 3 or 4.

12. A method for determining a concentration of GP2a, comprising:
   providing a sample having a complex comprising at least one affinity reagent directed against GP2a bound to said GP2a in a bodily fluid obtained from a human subject exhibiting symptoms of pancreatic disease, wherein said sample is obtained from the subject within 72 hours of appearance of said symptoms,
   wherein said sample shows that the concentration of GP2a of the human subject is greater than 0.7 ng/ml, wherein an acute pancreatitis (AP) specific treatment is administered to the subject whose sample has a concentration of GP2a that is greater than 0.7 ng/ml and the AP specific treatment or treatment regime differs from a treatment for chronic pancreatitis or pancreatic cancer.

13. The method according to claim 12, wherein the affinity reagent is bound to said GP2a and is not bound or negligibly bound to GP2b in the sample.

14. The method according to claim 12, wherein the affinity reagent is bound to said GP2a, wherein the GP2a comprises an amino acid sequence according to SEQ ID NO 1 or 2, and is not bound or negligibly bound to GP2b in the sample, wherein the GP2b comprises an amino acid sequence according to SEQ ID NO 3 or 4.

* * * * *

SEQUENCE LISTING

<160> NUMBER OF SEQ ID NOS: 8

<210> SEQ ID NO 1
<211> LENGTH: 537
<212> TYPE: PRT
<213> ORGANISM: Homo sapiens

<400> SEQUENCE: 1

Met Pro His Leu Met Glu Arg Met Val Gly Ser Gly Leu Leu Trp Leu
1               5                   10                  15

Ala Leu Val Ser Cys Ile Leu Thr Gln Ala Ser Ala Val Gln Arg Gly
            20                  25                  30

Tyr Gly Asn Pro Ile Glu Ala Ser Ser Tyr Gly Leu Asp Leu Asp Cys
        35                  40                  45

Gly Ala Pro Gly Thr Pro Glu Ala His Val Cys Phe Asp Pro Cys Gln
    50                  55                  60

Asn Tyr Thr Leu Leu Asp Glu Pro Phe Arg Ser Thr Glu Asn Ser Ala
65                  70                  75                  80

-continued

```
Gly Ser Gln Gly Cys Asp Lys Asn Met Ser Gly Trp Tyr Arg Phe Val
                85                  90                  95
Gly Glu Gly Gly Val Arg Met Ser Glu Thr Cys Val Gln Val His Arg
            100                 105                 110
Cys Gln Thr Asp Ala Pro Met Trp Leu Asn Gly Thr His Pro Ala Leu
        115                 120                 125
Gly Asp Gly Ile Thr Asn His Thr Ala Cys Ala His Trp Ser Gly Asn
    130                 135                 140
Cys Cys Phe Trp Lys Thr Glu Val Leu Val Lys Ala Cys Pro Gly Gly
145                 150                 155                 160
Tyr His Val Tyr Arg Leu Glu Gly Thr Pro Trp Cys Asn Leu Arg Tyr
                165                 170                 175
Cys Thr Val Pro Arg Asp Pro Ser Thr Val Glu Asp Lys Cys Glu Lys
            180                 185                 190
Ala Cys Arg Pro Glu Glu Cys Leu Ala Leu Asn Ser Thr Trp Gly
        195                 200                 205
Cys Phe Cys Arg Gln Asp Leu Asn Ser Ser Asp Val His Ser Leu Gln
    210                 215                 220
Pro Gln Leu Asp Cys Gly Pro Arg Glu Ile Lys Val Lys Val Asp Lys
225                 230                 235                 240
Cys Leu Leu Gly Gly Leu Gly Leu Gly Glu Glu Val Ile Ala Tyr Leu
                245                 250                 255
Arg Asp Pro Asn Cys Ser Ser Ile Leu Gln Thr Glu Glu Arg Asn Trp
            260                 265                 270
Val Ser Val Thr Ser Pro Val Gln Ala Ser Ala Cys Arg Asn Ile Leu
        275                 280                 285
Glu Arg Asn Gln Thr His Ala Ile Tyr Lys Asn Thr Leu Ser Leu Val
    290                 295                 300
Asn Asp Phe Ile Ile Arg Asp Thr Ile Leu Asn Ile Asn Phe Gln Cys
305                 310                 315                 320
Ala Tyr Pro Leu Asp Met Lys Val Ser Leu Gln Ala Ala Leu Gln Pro
                325                 330                 335
Ile Val Ser Ser Leu Asn Val Ser Val Asp Gly Asn Gly Glu Phe Ile
            340                 345                 350
Val Arg Met Ala Leu Phe Gln Asp Gln Asn Tyr Thr Asn Pro Tyr Glu
        355                 360                 365
Gly Asp Ala Val Glu Leu Ser Val Glu Ser Val Leu Tyr Val Gly Ala
    370                 375                 380
Ile Leu Glu Gln Gly Asp Thr Ser Arg Phe Asn Leu Val Leu Arg Asn
385                 390                 395                 400
Cys Tyr Ala Thr Pro Thr Glu Asp Lys Ala Asp Leu Val Lys Tyr Phe
                405                 410                 415
Ile Ile Arg Asn Ser Cys Ser Asn Gln Arg Asp Ser Thr Ile His Val
            420                 425                 430
Glu Glu Asn Gly Gln Ser Ser Glu Ser Arg Phe Ser Val Gln Met Phe
        435                 440                 445
Met Phe Ala Gly His Tyr Asp Leu Val Phe Leu His Cys Glu Ile His
    450                 455                 460
Leu Cys Asp Ser Leu Asn Glu Gln Cys Gln Pro Ser Cys Ser Arg Ser
465                 470                 475                 480
Gln Val Arg Ser Glu Val Pro Ala Ile Asp Leu Ala Arg Val Leu Asp
                485                 490                 495
```

```
Leu Gly Pro Ile Thr Arg Arg Gly Ala Gln Ser Pro Gly Val Met Asn
                500                 505                 510

Gly Thr Pro Ser Thr Ala Gly Phe Leu Val Ala Trp Pro Met Val Leu
        515                 520                 525

Leu Thr Val Leu Leu Ala Trp Leu Phe
        530                 535

<210> SEQ ID NO 2
<211> LENGTH: 534
<212> TYPE: PRT
<213> ORGANISM: Homo sapiens

<400> SEQUENCE: 2

Met Pro His Leu Met Glu Arg Met Val Gly Ser Gly Leu Leu Trp Leu
1               5                   10                  15

Ala Leu Val Ser Cys Ile Leu Thr Gln Ala Ser Ala Val Gln Arg Gly
                20                  25                  30

Tyr Gly Asn Pro Ile Glu Ala Ser Ser Tyr Gly Leu Asp Leu Asp Cys
            35                  40                  45

Gly Ala Pro Gly Thr Pro Glu Ala His Val Cys Phe Asp Pro Cys Gln
    50                  55                  60

Asn Tyr Thr Leu Leu Asp Glu Pro Phe Arg Ser Thr Glu Asn Ser Ala
65                  70                  75                  80

Gly Ser Gln Gly Cys Asp Lys Asn Met Ser Gly Trp Tyr Arg Phe Val
                85                  90                  95

Gly Glu Gly Gly Val Arg Met Ser Glu Thr Cys Val Gln Val His Arg
            100                 105                 110

Cys Gln Thr Asp Ala Pro Met Trp Leu Asn Gly Thr His Pro Ala Leu
    115                 120                 125

Gly Asp Gly Ile Thr Asn His Thr Ala Cys Ala His Trp Ser Gly Asn
    130                 135                 140

Cys Cys Phe Trp Lys Thr Glu Val Leu Val Lys Ala Cys Pro Gly Gly
145                 150                 155                 160

Tyr His Val Tyr Arg Leu Glu Gly Thr Pro Trp Cys Asn Leu Arg Tyr
                165                 170                 175

Cys Thr Asp Pro Ser Thr Val Glu Asp Lys Cys Glu Lys Ala Cys Arg
            180                 185                 190

Pro Glu Glu Glu Cys Leu Ala Leu Asn Ser Thr Trp Gly Cys Phe Cys
    195                 200                 205

Arg Gln Asp Leu Asn Ser Ser Asp Val His Ser Leu Gln Pro Gln Leu
    210                 215                 220

Asp Cys Gly Pro Arg Glu Ile Lys Val Lys Val Asp Lys Cys Leu Leu
225                 230                 235                 240

Gly Gly Leu Gly Leu Gly Glu Glu Val Ile Ala Tyr Leu Arg Asp Pro
                245                 250                 255

Asn Cys Ser Ser Ile Leu Gln Thr Glu Glu Arg Asn Trp Val Ser Val
            260                 265                 270

Thr Ser Pro Val Gln Ala Ser Ala Cys Arg Asn Ile Leu Glu Arg Asn
    275                 280                 285

Gln Thr His Ala Ile Tyr Lys Asn Thr Leu Ser Leu Val Asn Asp Phe
    290                 295                 300

Ile Ile Arg Asp Thr Ile Leu Asn Ile Asn Phe Gln Cys Ala Tyr Pro
305                 310                 315                 320

Leu Asp Met Lys Val Ser Leu Gln Ala Ala Leu Gln Pro Ile Val Ser
                325                 330                 335
```

```
Ser Leu Asn Val Ser Val Asp Gly Asn Gly Glu Phe Ile Val Arg Met
            340                 345                 350

Ala Leu Phe Gln Asp Gln Asn Tyr Thr Asn Pro Tyr Glu Gly Asp Ala
            355                 360                 365

Val Glu Leu Ser Val Glu Ser Val Leu Tyr Val Gly Ala Ile Leu Glu
            370                 375                 380

Gln Gly Asp Thr Ser Arg Phe Asn Leu Val Leu Arg Asn Cys Tyr Ala
385                 390                 395                 400

Thr Pro Thr Glu Asp Lys Ala Asp Leu Val Lys Tyr Phe Ile Ile Arg
            405                 410                 415

Asn Ser Cys Ser Asn Gln Arg Asp Ser Thr Ile His Val Glu Glu Asn
            420                 425                 430

Gly Gln Ser Ser Glu Ser Arg Phe Ser Val Gln Met Phe Met Phe Ala
            435                 440                 445

Gly His Tyr Asp Leu Val Phe Leu His Cys Glu Ile His Leu Cys Asp
            450                 455                 460

Ser Leu Asn Glu Gln Cys Gln Pro Ser Cys Ser Arg Ser Gln Val Arg
465                 470                 475                 480

Ser Glu Val Pro Ala Ile Asp Leu Ala Arg Val Leu Asp Leu Gly Pro
            485                 490                 495

Ile Thr Arg Arg Gly Ala Gln Ser Pro Gly Val Met Asn Gly Thr Pro
            500                 505                 510

Ser Thr Ala Gly Phe Leu Val Ala Trp Pro Met Val Leu Leu Thr Val
            515                 520                 525

Leu Leu Ala Trp Leu Phe
    530

<210> SEQ ID NO 3
<211> LENGTH: 390
<212> TYPE: PRT
<213> ORGANISM: Homo sapiens

<400> SEQUENCE: 3

Met Pro His Leu Met Glu Arg Met Val Gly Ser Gly Leu Leu Trp Leu
1               5                   10                  15

Ala Leu Val Ser Cys Ile Leu Thr Gln Ala Ser Ala Val Gln Arg Val
            20                  25                  30

Pro Arg Asp Pro Ser Thr Val Glu Asp Lys Cys Glu Lys Ala Cys Arg
            35                  40                  45

Pro Glu Glu Glu Cys Leu Ala Leu Asn Ser Thr Trp Gly Cys Phe Cys
50                  55                  60

Arg Gln Asp Leu Asn Ser Ser Asp Val His Ser Leu Gln Pro Gln Leu
65                  70                  75                  80

Asp Cys Gly Pro Arg Glu Ile Lys Val Lys Val Asp Lys Cys Leu Leu
            85                  90                  95

Gly Gly Leu Gly Leu Gly Glu Glu Val Ile Ala Tyr Leu Arg Asp Pro
            100                 105                 110

Asn Cys Ser Ser Ile Leu Gln Thr Glu Glu Arg Asn Trp Val Ser Val
            115                 120                 125

Thr Ser Pro Val Gln Ala Ser Ala Cys Arg Asn Ile Leu Glu Arg Asn
            130                 135                 140

Gln Thr His Ala Ile Tyr Lys Asn Thr Leu Ser Leu Val Asn Asp Phe
145                 150                 155                 160

Ile Ile Arg Asp Thr Ile Leu Asn Ile Asn Phe Gln Cys Ala Tyr Pro
```

```
                165                 170                 175
Leu Asp Met Lys Val Ser Leu Gln Ala Ala Leu Gln Pro Ile Val Ser
                180                 185                 190

Ser Leu Asn Val Ser Val Asp Gly Asn Gly Glu Phe Ile Val Arg Met
                195                 200                 205

Ala Leu Phe Gln Asp Gln Asn Tyr Thr Asn Pro Tyr Glu Gly Asp Ala
            210                 215                 220

Val Glu Leu Ser Val Glu Ser Val Leu Tyr Val Gly Ala Ile Leu Glu
225                 230                 235                 240

Gln Gly Asp Thr Ser Arg Phe Asn Leu Val Leu Arg Asn Cys Tyr Ala
                    245                 250                 255

Thr Pro Thr Glu Asp Lys Ala Asp Leu Val Lys Tyr Phe Ile Ile Arg
                260                 265                 270

Asn Ser Cys Ser Asn Gln Arg Asp Ser Thr Ile His Val Glu Glu Asn
                275                 280                 285

Gly Gln Ser Ser Glu Ser Arg Phe Ser Val Gln Met Phe Met Phe Ala
            290                 295                 300

Gly His Tyr Asp Leu Val Phe Leu His Cys Glu Ile His Leu Cys Asp
305                 310                 315                 320

Ser Leu Asn Glu Gln Cys Gln Pro Ser Cys Ser Arg Ser Gln Val Arg
                    325                 330                 335

Ser Glu Val Pro Ala Ile Asp Leu Ala Arg Val Leu Asp Leu Gly Pro
                340                 345                 350

Ile Thr Arg Arg Gly Ala Gln Ser Pro Gly Val Met Asn Gly Thr Pro
                355                 360                 365

Ser Thr Ala Gly Phe Leu Val Ala Trp Pro Met Val Leu Leu Thr Val
            370                 375                 380

Leu Leu Ala Trp Leu Phe
385                 390

<210> SEQ ID NO 4
<211> LENGTH: 387
<212> TYPE: PRT
<213> ORGANISM: Homo sapiens

<400> SEQUENCE: 4

Met Pro His Leu Met Glu Arg Met Val Gly Ser Gly Leu Leu Trp Leu
1               5                   10                  15

Ala Leu Val Ser Cys Ile Leu Thr Gln Ala Ser Ala Val Gln Arg Asp
                20                  25                  30

Pro Ser Thr Val Glu Asp Lys Cys Glu Lys Ala Cys Arg Pro Glu Glu
            35                  40                  45

Glu Cys Leu Ala Leu Asn Ser Thr Trp Gly Cys Phe Cys Arg Gln Asp
        50                  55                  60

Leu Asn Ser Ser Asp Val His Ser Leu Gln Pro Gln Leu Asp Cys Gly
65                  70                  75                  80

Pro Arg Glu Ile Lys Val Lys Val Asp Lys Cys Leu Leu Gly Gly Leu
                85                  90                  95

Gly Leu Gly Glu Glu Val Ile Ala Tyr Leu Arg Asp Pro Asn Cys Ser
            100                 105                 110

Ser Ile Leu Gln Thr Glu Glu Arg Asn Trp Val Ser Val Thr Ser Pro
        115                 120                 125

Val Gln Ala Ser Ala Cys Arg Asn Ile Leu Glu Arg Asn Gln Thr His
    130                 135                 140
```

Ala Ile Tyr Lys Asn Thr Leu Ser Leu Val Asn Asp Phe Ile Ile Arg
145                 150                 155                 160

Asp Thr Ile Leu Asn Ile Asn Phe Gln Cys Ala Tyr Pro Leu Asp Met
            165                 170                 175

Lys Val Ser Leu Gln Ala Ala Leu Gln Pro Ile Val Ser Ser Leu Asn
        180                 185                 190

Val Ser Val Asp Gly Asn Gly Glu Phe Ile Val Arg Met Ala Leu Phe
    195                 200                 205

Gln Asp Gln Asn Tyr Thr Asn Pro Tyr Glu Gly Asp Ala Val Glu Leu
210                 215                 220

Ser Val Glu Ser Val Leu Tyr Val Gly Ala Ile Leu Glu Gln Gly Asp
225                 230                 235                 240

Thr Ser Arg Phe Asn Leu Val Leu Arg Asn Cys Tyr Ala Thr Pro Thr
            245                 250                 255

Glu Asp Lys Ala Asp Leu Val Lys Tyr Phe Ile Ile Arg Asn Ser Cys
        260                 265                 270

Ser Asn Gln Arg Asp Ser Thr Ile His Val Glu Glu Asn Gly Gln Ser
    275                 280                 285

Ser Glu Ser Arg Phe Ser Val Gln Met Phe Met Phe Ala Gly His Tyr
290                 295                 300

Asp Leu Val Phe Leu His Cys Glu Ile His Leu Cys Asp Ser Leu Asn
305                 310                 315                 320

Glu Gln Cys Gln Pro Ser Cys Ser Arg Ser Gln Val Arg Ser Glu Val
            325                 330                 335

Pro Ala Ile Asp Leu Ala Arg Val Leu Asp Leu Gly Pro Ile Thr Arg
        340                 345                 350

Arg Gly Ala Gln Ser Pro Gly Val Met Asn Gly Thr Pro Ser Thr Ala
    355                 360                 365

Gly Phe Leu Val Ala Trp Pro Met Val Leu Leu Thr Val Leu Leu Ala
370                 375                 380

Trp Leu Phe
385

<210> SEQ ID NO 5
<211> LENGTH: 1614
<212> TYPE: DNA
<213> ORGANISM: Homo sapiens

<400> SEQUENCE: 5
atgcctcacc ttatggaaag gatggtgggc tctggcctcc tgtggctggc cttggtctcc      60
tgcattctga cccaggcatc tgcagtgcag cgaggttatg gaaacccat  tgaagccagt     120 tcgtatgggc tggacctgga ctgcggagct cctggcaccc cagaggctca tgtctgtttt     180 gaccctgtc agaattacac cctcctggat gaacccttcc gaagcacaga aactcagca      240 gggtcccagg ggtgcgataa aaacatgagc ggctggtacc gctttgtagg ggaaggagga    300
gtaaggatgt cggagacctg tgtccaggtg caccgatgcc agacagacgc tcccatgtgg    360
ctgaatggga cccacccttgc ccttggggat ggcatcacca accacactgc ctgtgcccat   420
tggagtggca actgctgttt ctggaaaaca gaggtgctgg tgaaggcctg cccaggcggg    480
taccatgtgt accggttgga aggcactccc tggtgtaatc tgagatactg cacagttcca    540
cgagacccat ccactgtgga ggacaagtgt gagaaggcct gccgccccga ggaggagtgc    600
cttgccctca cagcacctg gggctgtttc tgcagacagg acctcaatag ttctgatgtc     660
cacagtttgc agcctcagct agactgtggg cccagggaga tcaaggtgaa ggtggacaaa    720

```
tgtttgctgg gaggcctggg tttgggggag gaggtcattg cctacctgcg agacccaaac      780
tgcagcagca tcttgcagac agaggagagg aactgggtat ctgtgaccag ccccgtccag      840
gctagtgcct gcaggaacat tctggagaga aatcaaaccc atgccatcta caaaaacacc      900
ctctccttgg tcaatgattt catcatcaga gacaccatcc tcaacatcaa cttccaatgt      960
gcctacccac tggacatgaa agtcagcctc caagctgcct tgcagcccat tgtaagttcc     1020
ctgaacgtca gtgtggacgg gaatggagag ttcattgtca ggatggccct cttccaagac     1080
cagaactaca cgaatcctta cgaaggggat gcagttgaac tgtctgttga gtccgtgctg     1140
tatgtgggtg ccatcttgga acaaggggac acctcccggt ttaacctggt gttgaggaac     1200
tgctatgcca cccccactga agacaaggct gaccttgtga agtatttcat catcagaaac     1260
agctgctcaa atcaacgtga ttccaccatc acgtggagg agaatgggca gtcctcggaa      1320
agccggttct cagttcagat gttcatgttt gctggacatt atgacctagt tttcctgcat     1380
tgtgagattc atctctgtga ttctcttaat gaacagtgcc agccttcttg ctcaagaagt     1440
caagtccgca gtgaagtacc ggccatcgac ctagcccggg ttctagattt ggggcccatc     1500
actcggagag gtgcacagtc tcccggtgtc atgaatggaa cccctagcac tgcagggttc     1560
ctggtggcct ggcctatggt cctcctgact gtcctcctgg cttggctgtt ctga           1614

<210> SEQ ID NO 6
<211> LENGTH: 1605
<212> TYPE: DNA
<213> ORGANISM: Homo sapiens

<400> SEQUENCE: 6
atgcctcacc ttatggaaag gatggtgggc tctggcctcc tgtggctggc cttggtctcc       60
tgcattctga cccaggcatc tgcagtgcag cgaggttatg aaacccccat tgaagccagt      120
tcgtatgggc tggacctgga ctgcggagct cctggcaccc cagaggctca tgtctgtttt      180 gaccccctgtc agaattacac cctcctggat gaacccttcc gaagcacaga gaactcagca     240
gggtcccagg ggtgcgataa aaacatgagc ggctggtacc gctttgtagg ggaaggagga     300
gtaaggatgt cggagacctg tgtccaggtg caccgatgcc agacagacgc tcccatgtgg     360
ctgaatggga cccaccctgc ccttggggat ggcatcacca accacactgc ctgtgcccat     420
tggagtggca actgctgttt ctggaaaaca gaggtgctgg tgaaggcctg cccaggcggg     480
taccatgtgt accggttgga aggcactccc tggtgtaatc tgagatactg cacagaccca     540
tccactgtgg aggacaagtg tgagaaggcc tgccgccccg aggaggagtg ccttgccctc     600
aacagcacct ggggctgttt ctgcagacag gacctcaata gttctgatgt ccacagtttg     660
cagcctcagc tagactgtgg gcccaggag atcaaggtga aggtggacaa atgtttgctg     720
ggaggcctgg gtttggggga ggaggtcatt gcctacctgc gagacccaaa ctgcagcagc     780
atcttgcaga cagaggagag gaactgggta tctgtgacca gccccgtcca ggctagtgcc     840
tgcaggaaca ttctggagag aaatcaaacc catgccatct acaaaaacac cctctccttg     900
gtcaatgatt tcatcatcag agacaccatc ctcaacatca acttccaatg tgcctaccca     960
ctggacatga aagtcagcct ccaagctgcc ttgcagccca ttgtaagttc ctgaacgtc     1020 agtgtggacg ggaatggaga gttcattgtc aggatggccc tcttccaaga ccagaactac     1080
acgaatcctt acgaagggga tgcagttgaa ctgtctgttg agtccgtgct gtatgtgggt     1140
gccatcttgg aacaagggga cacctcccgg tttaacctgg tgttgaggaa ctgctatgcc     1200
```

| | |
|---|---:|
| accccccactg aagacaaggc tgaccttgtg aagtatttca tcatcagaaa cagctgctca | 1260 |
| aatcaacgtg attccaccat ccacgtggag gagaatgggc agtcctcgga aagccggttc | 1320 |
| tcagttcaga tgttcatgtt tgctggacat tatgacctag ttttcctgca ttgtgagatt | 1380 |
| catctctgtg attctcttaa tgaacagtgc cagccttctt gctcaagaag tcaagtccgc | 1440 |
| agtgaagtac cggccatcga cctagcccgg gttctagatt tggggcccat cactcggaga | 1500 |
| ggtgcacagt ctcccggtgt catgaatgga acccctagca ctgcagggtt cctggtggcc | 1560 |
| tggcctatgg tcctcctgac tgtcctcctg gcttggctgt tctga | 1605 |

<210> SEQ ID NO 7
<211> LENGTH: 1173
<212> TYPE: DNA
<213> ORGANISM: Homo sapiens

<400> SEQUENCE: 7

| | |
|---|---:|
| atgcctcacc ttatggaaag gatggtgggc tctggcctcc tgtggctggc cttggtctcc | 60 |
| tgcattctga cccaggcatc tgcagtgcag cgagttccac gagacccatc cactgtggag | 120 |
| gacaagtgtg agaaggcctg ccgccccgag gaggagtgcc ttgccctcaa cagcacctgg | 180 |
| ggctgttttct gcagacagga cctcaatagt tctgatgtcc acagtttgca gcctcagcta | 240 |
| gactgtgggc ccagggagat caaggtgaag gtggacaaat gtttgctggg aggcctgggt | 300 |
| ttgggggagg aggtcattgc ctacctgcga gacccaaact gcagcagcat cttgcagaca | 360 |
| gaggagagga actgggtatc tgtgaccagc ccgtccagg ctagtgcctg caggaacatt | 420 |
| ctggagaaa atcaaaccca tgccatctac aaaaacaccc tctccttggt caatgatttc | 480 |
| atcatcagag acaccatcct caacatcaac ttccaatgtg cctacccact ggacatgaaa | 540 |
| gtcagcctcc aagctgcctt gcagcccatt gtaagttccc tgaacgtcag tgtgacgggg | 600 |
| aatggagagt tcattgtcag gatggccctc ttccaagacc agaactacac gaatccttac | 660 |
| gaaggggatg cagttgaact gtctgttgag tccgtgctgt atgtgggtgc catcttggaa | 720 |
| caaggggaca cctcccggtt taacctggtg ttgaggaact gctatgccac ccccactgaa | 780 |
| gacaaggctg accttgtgaa gtatttcatc atcagaaaca gctgctcaaa tcaacgtgat | 840 |
| tccaccatcc acgtggagga gaatgggcag tcctcggaaa gccggttctc agttcagatg | 900 |
| ttcatgtttg ctggacatta tgacctagtt ttcctgcatt gtgagattca tctctgtgat | 960 |
| tctcttaatg aacagtgcca gccttcttgc tcaagaagtc aagtccgcag tgaagtaccg | 1020 |
| gccatcgacc tagcccgggt tctagatttg ggcccatca ctcggagagg tgcacagtct | 1080 |
| cccggtgtca tgaatggaac ccctagcact gcagggttcc tggtggcctg gcctatggtc | 1140 |
| ctcctgactg tcctcctggc ttggctgttc tga | 1173 |

<210> SEQ ID NO 8
<211> LENGTH: 1164
<212> TYPE: DNA
<213> ORGANISM: Homo sapiens

<400> SEQUENCE: 8

| | |
|---|---:|
| atgcctcacc ttatggaaag gatggtgggc tctggcctcc tgtggctggc cttggtctcc | 60 |
| tgcattctga cccaggcatc tgcagtgcag cgagacccat ccactgtgga ggacaagtgt | 120 |
| gagaaggcct gccgccccga ggaggagtgc cttgccctca acagcacctg ggctgtttc | 180 |
| tgcagacagg acctcaatag ttctgatgtc cacagtttgc agcctcagct agactgtggg | 240 |
| cccagggaga tcaaggtgaa ggtggacaaa tgtttgctgg gaggcctggg tttgggggag | 300 |

```
gaggtcattg cctacctgcg agacccaaac tgcagcagca tcttgcagac agaggagagg    360
aactgggtat ctgtgaccag ccccgtccag gctagtgcct gcaggaacat tctggagaga    420
aatcaaaccc atgccatcta caaaaacacc ctctccttgg tcaatgattt catcatcaga    480
gacaccatcc tcaacatcaa cttccaatgt gcctacccac tggacatgaa agtcagcctc    540
caagctgcct tgcagcccat tgtaagttcc ctgaacgtca gtgtggacgg gaatggagag    600
ttcattgtca ggatggccct cttccaagac cagaactaca cgaatcctta cgaaggggat    660
gcagttgaac tgtctgttga gtccgtgctg tatgtgggtg ccatcttgga acaaggggac    720
acctcccggt ttaacctggt gttgaggaac tgctatgcca cccccactga agacaaggct    780
gaccttgtga agtatttcat catcagaaac agctgctcaa atcaacgtga ttccaccatc    840
cacgtggagg agaatgggca gtcctcggaa agccggttct cagttcagat gttcatgttt    900
gctggacatt atgacctagt tttcctgcat tgtgagattc atctctgtga ttctcttaat    960
gaacagtgcc agccttcttg ctcaagaagt caagtccgca gtgaagtacc ggccatcgac   1020
ctagcccggg ttctagattt ggggcccatc actcggagag gtgcacagtc tcccggtgtc   1080
atgaatggaa cccctagcac tgcagggttc ctggtggcct ggcctatggt cctcctgact   1140
gtcctcctgg cttggctgtt ctga                                           1164
```